(12) United States Patent
Scifert et al.

(10) Patent No.: US 8,523,869 B2
(45) Date of Patent: Sep. 3, 2013

(54) PATELLO-FEMORAL JOINT IMPLANT AND INSTRUMENTATION

(75) Inventors: Christopher F. Scifert, Bartlett, TN (US); Jason S. Jordan, Hanando, MS (US); John H. Newman, Bristol (GB); William B. Smith, Milwaukee, WI (US)

(73) Assignee: Smith & Nephew, Inc., Memphis, TN (US)

( * ) Notice: Subject to any disclaimer, the term of this patent is extended or adjusted under 35 U.S.C. 154(b) by 1620 days.

(21) Appl. No.: 11/915,131

(22) Filed: Nov. 20, 2007

(65) Prior Publication Data

US 2012/0259335 A1    Oct. 11, 2012

Related U.S. Application Data

(63) Continuation of application No. PCT/US2006/019512, filed on May 19, 2006.

(60) Provisional application No. 60/683,289, filed on May 20, 2005.

(51) Int. Cl.
*A61F 2/64* (2006.01)

(52) U.S. Cl.
USPC .............................................. 606/88; 606/96

(58) Field of Classification Search
USPC ................. 623/20.14, 20.18, 20.19, 20.35
See application file for complete search history.

(56) References Cited

U.S. PATENT DOCUMENTS

| | | | |
|---|---|---|---|
| 4,007,495 A | 2/1977 | Frazier | |
| 5,035,699 A * | 7/1991 | Coates | 606/86 R |
| 5,098,436 A * | 3/1992 | Ferrante et al. | 606/88 |
| 5,702,459 A | 12/1997 | Hummer et al. | |
| 5,824,098 A * | 10/1998 | Stein | 623/20.18 |
| 6,482,209 B1 * | 11/2002 | Engh et al. | 606/79 |
| 6,616,696 B1 * | 9/2003 | Merchant | 623/20.18 |
| 7,678,115 B2 * | 3/2010 | D'Alessio et al. | 606/88 |
| 7,695,477 B2 | 4/2010 | Creger et al. | |
| 7,766,913 B2 * | 8/2010 | Bennett et al. | 606/86 R |
| 7,806,898 B2 * | 10/2010 | Justin et al. | 606/88 |
| 7,896,922 B2 * | 3/2011 | Engh et al. | 623/20.18 |
| 7,942,879 B2 * | 5/2011 | Christie et al. | 606/79 |

(Continued)

FOREIGN PATENT DOCUMENTS

| | | |
|---|---|---|
| AU | 199713876 A | 8/1997 |
| AU | 2005200304 B2 | 12/2006 |

(Continued)

OTHER PUBLICATIONS

International Search Report for International Application PCT/US2006/019512, mailed May 7, 2007.

(Continued)

*Primary Examiner* — Matthew Lawson
(74) *Attorney, Agent, or Firm* — Fish & Richardson P.C.

(57) ABSTRACT

A system for preparing a trochlear region of a resected femur is disclosed. The system includes a reamer guide and a reamer. The reamer guide has a first arcuate portion, a second arcuate portion, a wall, a protrusion connected to the wall, a leg connected to one of the first or second arcuate portion, and a distal tip portion connected to the leg. The reamer is adapted to rotatably connect to the distal tip portion, and the reamer has a first end portion, a second end portion, and one or more flutes.

19 Claims, 22 Drawing Sheets

(56) References Cited

U.S. PATENT DOCUMENTS

| | | | |
|---|---|---|---|
| 8,157,867 B2 * | 4/2012 | Goble et al. | 623/20.15 |
| 8,211,113 B2 * | 7/2012 | Brown et al. | 606/96 |
| 8,226,726 B2 | 7/2012 | Abendschein | |
| 2002/0019649 A1 | 2/2002 | Sikora et al. | |
| 2003/0236521 A1 * | 12/2003 | Brown et al. | 606/80 |
| 2004/0167630 A1 | 8/2004 | Rolston | |
| 2005/0143833 A1 * | 6/2005 | Merchant | 623/20.31 |
| 2006/0058884 A1 * | 3/2006 | Aram et al. | 623/20.15 |
| 2006/0276796 A1 * | 12/2006 | Creger et al. | 606/79 |
| 2009/0209962 A1 * | 8/2009 | Jamali | 606/81 |
| 2010/0222782 A1 | 9/2010 | Collazo et al. | |
| 2012/0165821 A1 | 6/2012 | Carignan et al. | |

FOREIGN PATENT DOCUMENTS

| | | | |
|---|---|---|---|
| CA | 2051736 | C | 1/1995 |
| DE | 3305237 | A1 | 8/1983 |
| DE | 20303643 | U1 | 8/2003 |
| EP | 687448 | A1 | 12/1995 |
| EP | 685210 | B1 | 11/1999 |
| EP | 1444959 | A1 | 8/2004 |
| EP | 1522265 | A1 | 4/2005 |
| FR | 2740326 | A1 | 4/1997 |
| GB | 1515382 | A | 6/1978 |
| JP | 2005111274 | A | 4/2005 |
| MX | 1994PA009154 | A | 3/2005 |
| WO | WO9104715 | A1 | 4/1991 |
| WO | WO9729704 | A1 | 8/1997 |
| WO | WO9743985 | A1 | 11/1997 |
| WO | WO0156481 | A1 | 8/2001 |
| WO | WO0170142 | A1 | 9/2001 |
| WO | WO03068119 | A2 | 8/2003 |
| WO | WO03013339 | A3 | 10/2003 |

OTHER PUBLICATIONS

Examiner's First Report on Australian Patent Application No. 2006261843, mailed Jan. 21, 2011, 2 pages.

Notice of Reasons for Rejection for Japanese Application No. 2011-148241, mailed Feb. 19, 2013.

Examination Report for Canadian Application No. 2,609,144, mailed Sep. 18, 2012.

* cited by examiner

PATELLO-FEMORAL JOINT IMPLANT AND INSTRUMENTATION

CROSS-REFERENCE TO RELATED APPLICATIONS

This application is a continuation of and claims the benefit of priority of International Application No. PCT/US2006/019512, filed May 19, 2006, which claims the benefit of U.S. Provisional Application No. 60/683,289, filed May 20, 2005.

BACKGROUND OF THE INVENTION

1. Field of the Invention

This invention relates generally to orthopaedic devices and more particularly to patello-femoral joint implants and instrumentation.

2. Related Art

The knee joint is a frequent place for joint damage, and the loss of normal (i.e., relatively pain-free) ambulatory function is a frequent result of such damage. Many different causes, or combination of causes, result in knee joint damage. For example, a modest overextension of a knee weakened by osteoporosis can result in damage. Moreover, the extent of the damage to the knee joint can vary greatly depending on the cause, age of the patient, pre-existing conditions and other factors.

The knee is a common source of problems because the joint has an unusually large range of motion and bears nearly half of the weight of the entire body. A primary knee movement, known as flexion-extension movement, includes bending (flexion) and straightening (extension) of the leg in which a lower part of the leg (tibia and fibula bones) flexes in relation to an upper part of the leg (femur bone). Ideally, the knee joint is capable of almost 180 degrees of flexion-extension movement. The knee joint can also accommodate a certain amount of rotational motion in which the lower leg rotates a few degrees in relation to the upper leg. This wide range of motion requires extensive contact surface between the femur and the tibia. Further, the knee joint is rather loosely held together by tendons and ligaments to permit such a wide range of motion.

The front, or anterior side, of the knee joint is protected by the knee cap or patella. The patella is held in place by ligaments and slides over a femoral joint surface during flexion-extension movement. The patella and its ligaments are mechanically involved in joint extension. If any of the joint surfaces (e.g., femoral surface, patellar surface, or tibial surface) becomes damaged or roughened, the knee joint will not operate properly and the patient is likely to experience significant pain.

A common problem is damage to the patello-femoral joint that causes free motion of the patella to be inhibited and/or painful. Such damage is sometimes referred to as "runner's knee." Patello-femoral joint (PFJ) damage can make normal joint movement almost impossible.

A variety of prosthetic replacements have been developed for different joint surfaces of the knee joint. In extreme cases, the entire joint can be replaced with a prosthetic device. Such a prosthetic replacement is referred to as a total knee replacement. However, total knee replacement requires a considerable time for recovery, and it may be advantageous to replace only the damaged part of the joint in less extreme cases.

In some cases, PFJ damage may be adequately addressed with a PFJ arthroplasty, as opposed to a total knee replacement system. This type of knee surgery is less drastic than total knee replacement. It is designed for patients whose main problems involve only the patello-femoral part of the knee and is directed to providing a smooth sliding relationship between the femur and the patella. The surface of the femur on which the patella slides is referred to as the trochlear groove. The trochlear groove is the indentation or groove located between the medial and lateral condylar surfaces at the distal end of the femur.

In prior art PFJ prosthetic systems, a prosthetic patellar bearing surface is introduced. The prosthetic bearing surface typically includes an anchoring portion for receiving natural patellar remnants. As a result, the final patellar structure includes a posterior prosthetic bearing surface and an anterior natural patella surface. The anterior natural patella surface typically retains the connective tissue that connects the patella to the quadriceps and tibia.

In order to achieve adequate translational movement of the prosthetic patellar bearing surface, particularly in the presence of damage to the trochlear groove, a cooperating prosthetic femur implant is typically affixed onto the end of the femur. The prosthetic femur implant in most cases includes a bearing surface that is specially adapted to receive the prosthetic patellar bearing surface to ensure reliable travel during flexion movement.

Such prior art systems, however, are typically highly artificial systems that employ unnatural patello-femoral tracking or movement of the patella. One drawback of such systems is that they are not compatible with total knee replacement systems. In many cases, the PFJ system requires so significant an amount of bone removal as to render subsequent total knee replacement almost impossible.

More natural patellar devices employ a saddle-shaped design. The saddle-shaped design may be used with or without a femoral implant and is intended to track the within the natural trochlear groove.

There is a need, therefore, for a patello-femoral prosthesis having the advantages of more naturally tracking designs. There is a further need for a femoral implant that requires less bone removal for implantation.

SUMMARY OF THE INVENTION

It is in view of the above problems that the present invention was developed. The invention is a patello-femoral joint implant and associated instrumentation. The implant resurfaces only the patello-femoral compartment of the knee and leaves the rest of the knee intact. The implant utilizes asymmetric components and a lateralized patellar groove to improve patellar tracking The instrumentation allows the device to be implanted through a minimally invasive approach without extensive damage to the quadriceps mechanism. A key feature of the instrumentation system is the reaming system which allows for reproducible preparation of the trochlear region of the femur.

In one aspect of the invention, there is a system for preparing a trochlear region of a resected femur, the system comprising: a reamer guide, the reamer guide having a first arcuate portion, a second arcuate portion, a wall extending therebetween, a protrusion connected to the wall, at least one leg connected to one of the first arcuate portion or the second arcuate portion, and a distal tip portion connected to the leg; and a reamer adapted to rotatably connect to the distal tip portion of the reamer guide, the reamer having a first end portion, a second end portion, and at least one flute.

In another aspect of the invention, there is a patello-femoral joint implant, the implant comprising: an intracondylar notch portion, a proximal portion, and a distal portion; an upper surface extending from the intracondylar notch portion to the proximal portion, the upper surface having a medial portion and a lateral portion; a lateralized groove forming a curved outer surface in between the medial portion and the lateral portion; a substantially planar undersurface connected to the intracondylar notch portion and opposite the upper surface; at least one anterior peg connected to the substantially planar undersurface; and at least one distal peg (19) connected to the substantially planar undersurface (16).

The invention has several advantages over prior devices and techniques. First, the implant has an asymmetric patellar track to provide better coverage of the anterior femur. The patellar track is lateralized to improve patellar tracking The natural patella tracks lateral to medial as the knee flexes. Other devices generate this tracking by rotating the component and angling a straight patellar track. This can lead to the patella moving too far medial and lead to unfavorable tracking. The implant assures proper central placement of the patella in flexion.

Second, the instrumentation is designed for a minimally invasive approach. A minimally invasive approach provides several advantages to the patient, including, among other things, a shorter recovery period and reduced pain. The instruments for all prior art systems are not designed for a minimally invasive approach.

Third, the reaming system allows for reproducible trochlear preparation and aids in proper alignment of the implant. Most prior art systems are not precise and rely on some kind of free-hand preparation of the trochlear and/or anterior region of the femur. This leads to inaccurate preparation and mal-rotation of the components, which is the second leading cause of failure in these devices. The reaming system also allows for a more uniform cement mantle than hand preparation would allow which may help prevent cement fatigue and loosening.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention, hi the drawings.

DETAILED DESCRIPTION OF THE PREFERRED EMBODIMENTS

Figure 1:
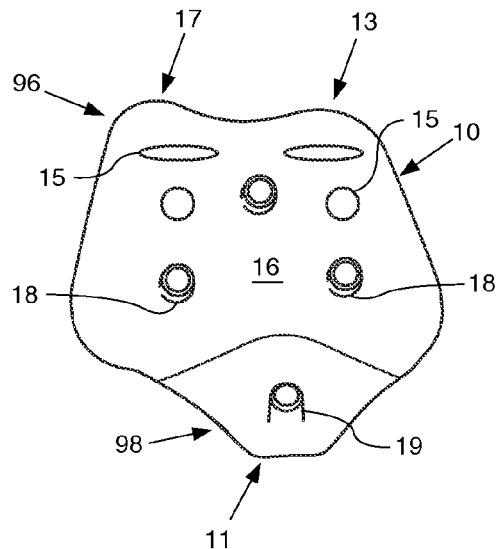
FIG. 1 is a posterior view of a patello-femoral implant.
Figure 3:
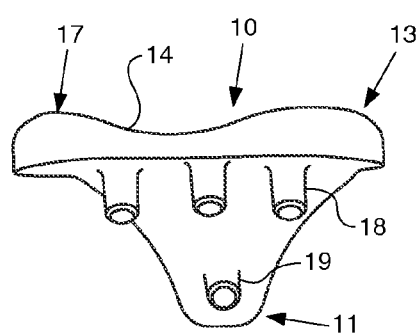
FIG. 3 is a proximal view of the patello-femoral implant shown in FIG. 1.
Figure 2:
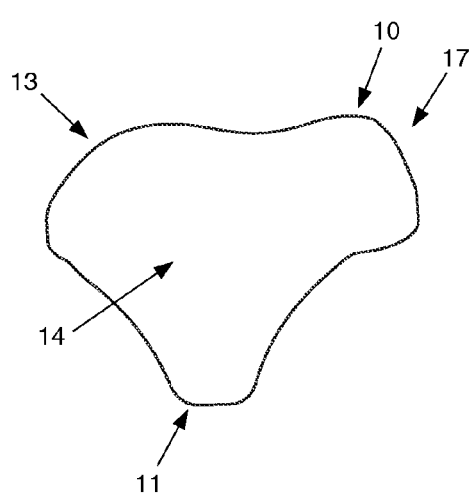
FIG. 2 is a distal view of the patello-femoral implant shown in FIG. 1.

Referring to the accompanying drawings in which like reference numbers indicate like elements, FIGS. 1-4 illustrate a patello-femoral implant 10. The implant 10 may be made from any biocompatible material. As examples, the implant 10 may be made from cobalt chromium, stainless steel, titanium, oxidized zirconium, other metal alloys, standard polyethylene, cross-linked polyethylene, ultra high molecular weight plastic, other plastics, or a composite material. The implant 10 resurfaces the patello-femoral region of the knee to alleviate the pain from patello-femoral arthritis. The implant 10 may be used with an unresurfaced patella (i.e., natural patella) or with any resurfaced patella implant, such as a dome-shaped patella implant or an oval patella implant.

The implant 10 includes an intracondylar notch portion 11, a medial portion 13, an upper surface 14, and a lateral portion 17. The implant 10 also includes a proximal portion or region 96 and a distal portion or region 98. The upper surface, or implant anterior surface, 14 extends from the intracondylar notch portion 11 to the proximal portion 96. The intracondylar notch portion 11 is constructed and arranged to provide a smooth transition to the femoral condyles. In some embodiments, the medial portion 13 and the lateral portion 17 are shaped to provide maximum bone coverage of the anterior femur. The lateral portion 17 has an increased thickness in the proximal region 96 to prevent patellar subluxation. In some embodiments, the medial portion 13 has less material than the lateral portion 17 in the proximal region 96. This may be done for several reasons. For example, the medial portion 13 may have less material in order to decrease the overall size of the implant 10, to reduce the weight of the implant 10, or to allow the implant 10 to achieve a better fit.

Figure 4:
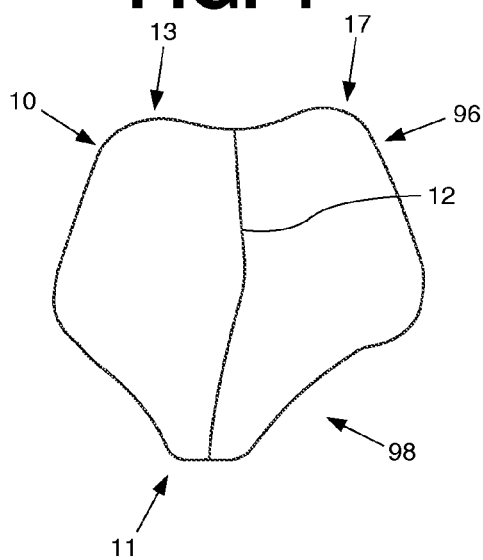
FIG. 4 is a anterior view of the patello-femoral implant shown in FIG. 1.
Figure 5:
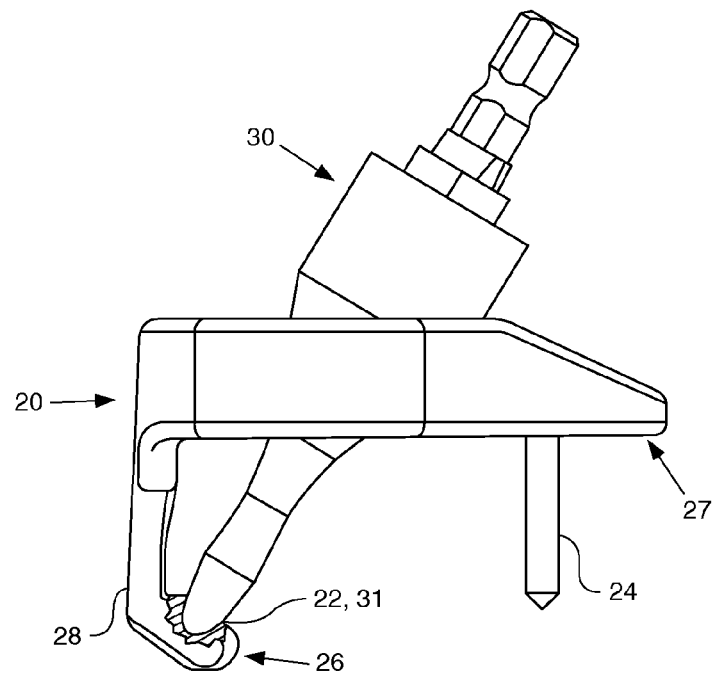
FIG. 5 is a side view of a first embodiment of a reamer guide and a first embodiment of a reamer.
Figure 6:
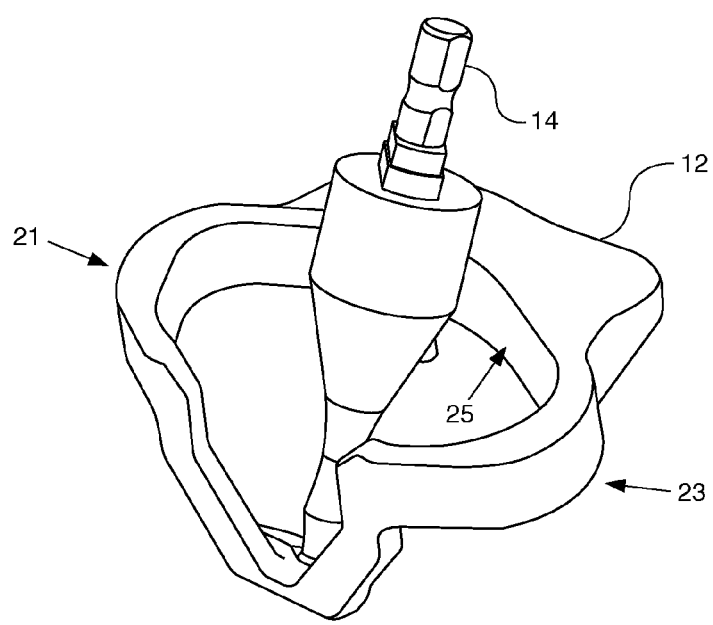
FIG. 6 is a perspective top view of the reamer guide and the reamer in a first position.
Figure 7:
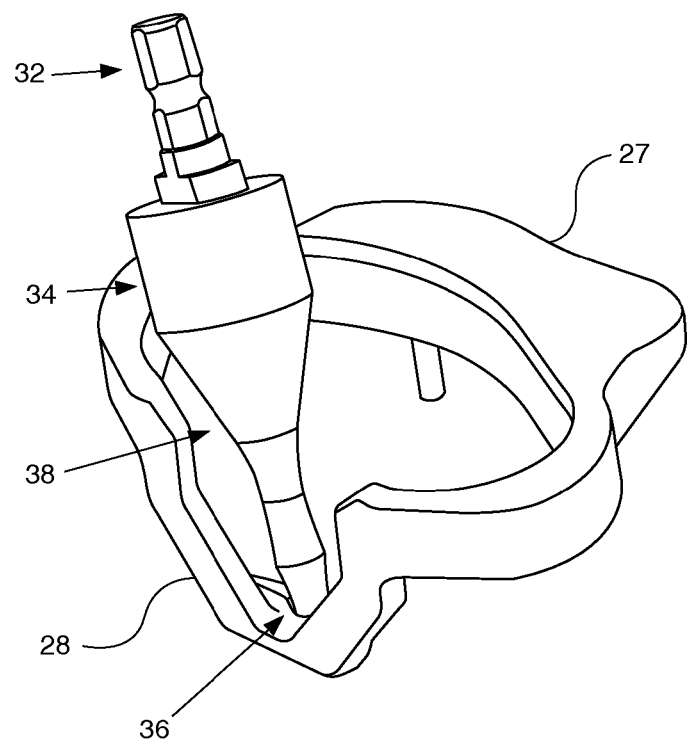
FIG. 7 is a perspective top view of the reamer guide and the reamer in a second position.
Figure 8:
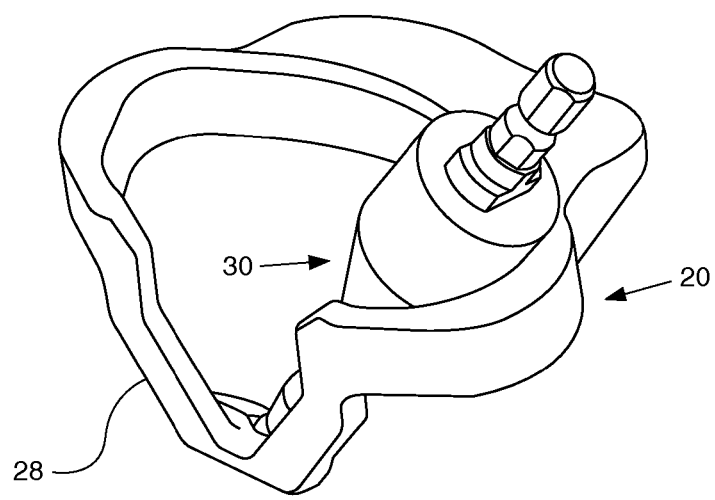
FIG. 8 is a perspective top view of the reamer guide and the reamer in a third position.

As best seen in FIG. 4, the implant 10 has a lateralized patello-femoral groove 12. In the embodiment depicted in FIG. 4, the black line represents a central area or average location of the groove 12, but those of ordinary skill in the art would understand that the black line is merely representative of location and the actual shape of the groove is such that an unresurfaced or resurfaced patella may track within it. The groove 12 forms a curved outer surface, or bearing surface, in which the patella tracks. The groove 12 is lateralized in the proximal region 96 to allow the patella to track normally, regardless of whether the patella has been resurfaced or not. The patella is lateralized in extension and transitions to the intracondylar notch portion 11 in flexion as it moves in the groove 12.

Figure 31:
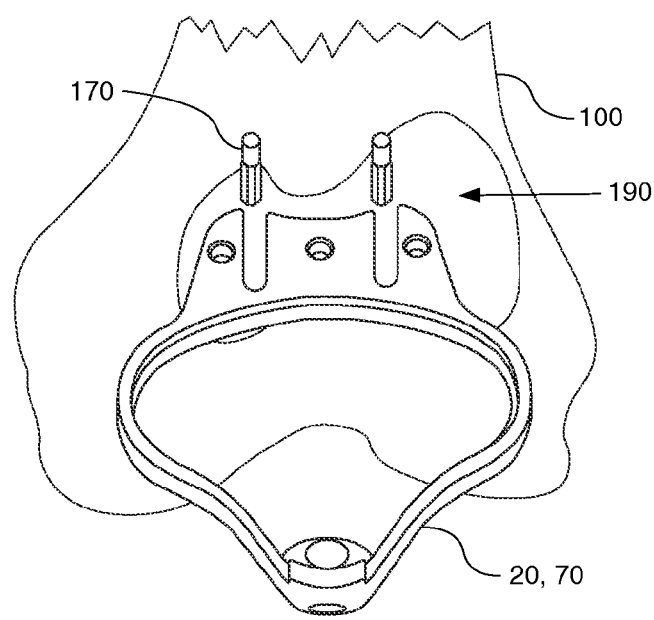
FIG. 31 is a top perspective view of the femur and a second embodiment of a reamer guide.
Figure 32:
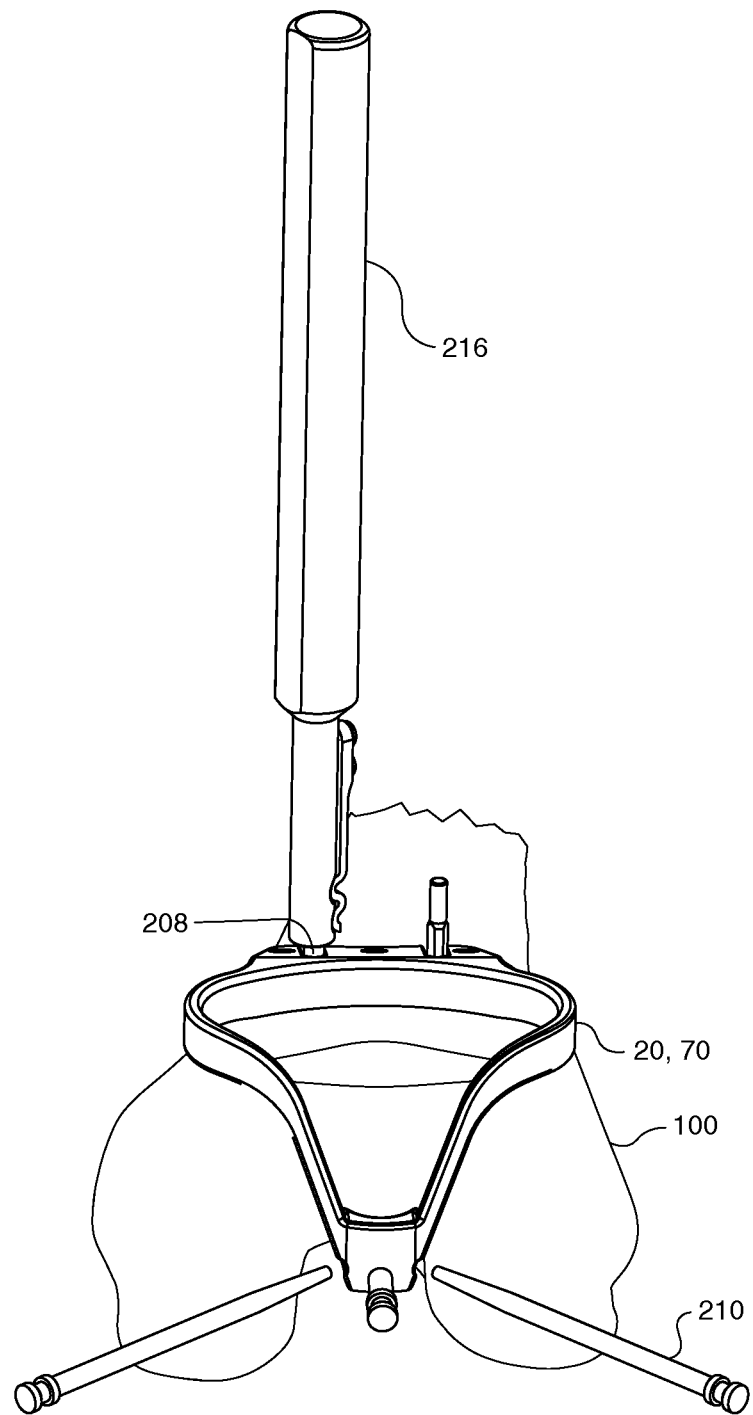
FIG. 32 is a front perspective view of the femur, the second embodiment of the reamer guide, and a plurality of fixation devices.

The implant 10 includes a substantially planar anterior under-surface 16 for placement on a generally flat or planar anterior cut 190 (best seen in FIG. 31) on a femur 100. The substantially planar anterior under-surface, or implant posterior surface, 16 is located opposite the upper surface 14. The substantially planar anterior under-surface 16 may be parallel to the coronal plane, or the anterior under-surface 16 may be sloped to prevent stress shielding. In other words, some embodiments of the implant 10 are sloped, or shaped, such that a force upon the groove 12 tends to push the implant 10 towards the anatomic axis of the femur and not along the anatomic axis. The anterior under-surface 16 may be sloped in the range from about one degree to about ten degrees relative to the coronal plane in order to prevent stress shielding. In the embodiment depicted in FIG. 1, the anterior under-surface 16 slopes at about three degrees.

In some embodiments, the anterior under-surface 16 includes features to enhance its use with bone cement. For example, the anterior under-surface 16 may be grit blasted to roughen the surface or may include indentations, pockets, depressions, or dimples 15. The dimples 15 may be elongated cavities, circular depressions, rectangular voids, triangular cavities, or any other shape of indentation.

The implant 10 includes anterior anchors or pegs 18 and, in some embodiments, distal peg or pegs 19. In the embodiment depicted in FIGS. 1 and 3, the implant 10 has three anterior pegs 18 and one distal peg 19, but those of ordinary skill in the art would understand that a greater or lesser number of pegs may be used. As examples, in some embodiments, the distal peg 19 may be omitted entirely or the implant 10 may include a plurality of distal pegs 19. The distal peg 19 may be angled relative to the anterior pegs 18 to enhance cement fixation. In the embodiment depicted in FIG. 1, the distal peg 19 is oblique relative to the anterior pegs 18. The oblique angle of the distal peg 19 allows for a snap fit of the implant 10.

FIGS. 5-8 illustrate a first embodiment of a reamer guide 20 and a first embodiment of a reamer 30. The reamer guide 20 and the reamer 30 reproducibly ream the trochlear region of the femur 100 to allow for installation of the implant 10. The reamer guide 20 is small and medially biased to allow for insertion into a small incision, such as is used in minimally invasive surgery (MIS). The reamer guide 20 may be adapted for use on a left knee, a right knee, or either knee. In the depicted embodiments, the reamer guide 20 is adapted for use on either knee. The reamer guide 20 is adapted to attach to the resected anterior surface 190. The reamer guide 20 further includes a first arcuate portion 21, a second arcuate portion 23, a wall 25, a protrusion 27, at least one locating member 24, a leg 28, a distal tip portion 26, and a nearly-spherical indentation or a more-than-hemispherical depression 22. The wall 25 is connected to the first arcuate portion 21, the second arcuate portion 23, and the protrusion 27. The shape of the wall 25 is constructed and arranged such that it follows an outline of the underside of the implant 10. The locating member 24 extends from an underside of the protrusion 27. The leg 28 is connected to the first arcuate portion 21 and the second arcuate portion 23. In the depicted embodiments, the leg 28 is V-shaped but other shapes may be used. The distal tip portion 26 is connected to the leg 28, and the more-than-hemispherical depression 22 is located in the distal tip portion 26.

In some embodiments, the first and second arcuate portions 21, 23 are sized and located to limit the amount of medial and lateral resection. As such, the first arcuate portion 21, the second arcuate portion 23, and the wall 25 control the shape and depth of resection of the trochlear region. In other embodiments, the first and second arcuate portions 21, 23 are merely structural members that connect the leg 28 to the other components of the reamer guide 20, and, therefore, the user must exercise caution to ensure that the trochlear region is not over-resected medially or laterally.

The reamer 30, alternatively termed a mill, is a somewhat hourglass shaped cutting instrument. In some embodiments, the reamer 30 is adapted for use with a standard drill. The reamer 30 has a connector 31 that is housed by a more-than-hemispherical depression or over-hemispherical depression 22 in the reamer guide 20. In the depicted embodiments, the connector 31 is spherical or has a ball nose shape. The distal part of the reamer 30 is housed in the hemispherical indentation, and the proximal part is leaned against the reamer guide 20 and slid medio-laterally to ream the trochlear region. The reamer 30 also includes a first end portion 32, a bearing 34, a second end portion 36, and at least one tooth or flute 38. As the bearing 34 decreases in size, the deeper the reamer 30 will ream the trochlear region, and as the bearing increases in size, the shallower the reamer 30 will ream the trochlear region. Alternatively, the teeth 38 may increase in size such that additional bone is reamed. Thus, the reamer 30 may be available in different versions with a correspondingly sized bearing 34 or teeth 38 such that a particular size of reamer is chosen according to the desired amount of reaming. A kit of differently sized reamers and a reamer guide may be provided.

In use, the reamer guide 20 is mounted to the distal end of a resected femur. A user inserts the distal tip 31 into the over-hemispherical depression 22. The user levers or pivots the reamer 30 downward onto the reamer guide 20, resecting bone as the reamer 30 is pivoted. The reamer 30 is pivoted until the bearing 34 rides on or rotates against the wall 25. The reamer 30 is then moved medial-to-lateral, or vice versa, to prepare the trochlear region.

Figure 9:
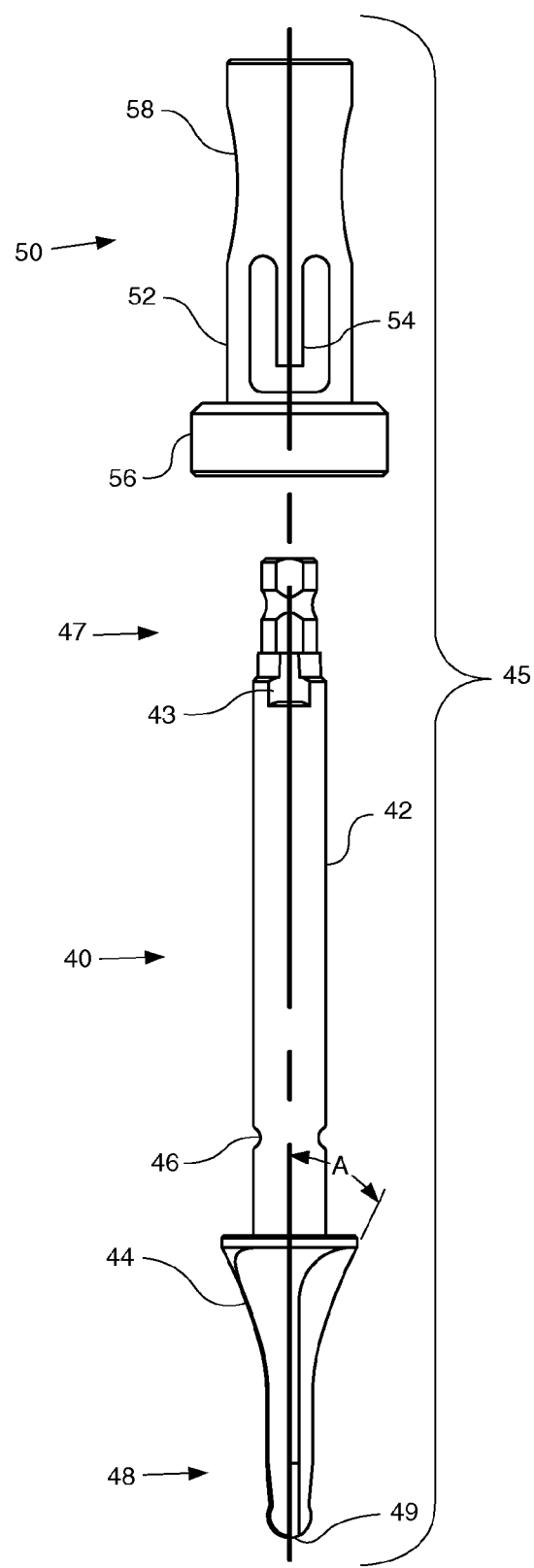
FIG. 9 is an exploded view of a first embodiment of a reamer sleeve and a second embodiment of the reamer.

FIG. 9 illustrates a second embodiment of the reamer, generally indicated by reference numeral 40, and a first embodiment of a reamer sleeve 50. The reamer 40 and the sleeve 50 are assembled together to form a reamer assembly 45. The reamer 40 may also be referred to as a mill. The reamer 40 has a shaft 42, at least one tooth or flute 44, a first end portion 47, and a second end portion 48. Optionally, the reamer 40 may also include a groove or channel 46 located on the shaft 42. In some embodiments, a profile of the flute 44 is shaped to match the underside of the implant 10. In the embodiment depicted in FIG. 9, the reamer 40 has four flutes 44, but those of ordinary skill in the art would understand that a greater or lesser number of flutes may be used. The flute 44 has a relief angle A which ranges from about five degrees to about thirty-five degrees. In the embodiment depicted in FIG. 9, the relief angle A is about twenty degrees. The second end portion 48 may have any number of shapes and is adapted to rotatably connect to the reamer guide. In the embodiment depicted in FIG. 9, the second end portion 48 terminates in a connector 49 which has a substantially hemispherical shape. The first end portion 47 also may have any number of shapes but in the depicted embodiment has three circumferentially spaced, planar surfaces 43 adapted for use or engagement with a drill chuck (not shown).

In some embodiments, the reamer guide 20 and the reamer 30, 40 may be one piece. For example, the reamer guide 20 may include a rotatable bearing, such as a spherical bearing, and the reamer 30, 40 may rotate within this bearing.

The reamer 40 is adapted to receive the sleeve 50. The sleeve 50 includes a main body 52, at least one arm 54, and a bearing or platform 56. The sleeve 50 may be made from a metal, such as stainless steel, a plastic, such as an acetal copolymer, or a composite material. Optionally, the main body 52 may include a grip portion 58. The grip portion 58 provides a convenient place for the user to place his or her thumb and forefinger. The reamer sleeve 50 is used to control the depth that the reamer 40 engages the trochlear region. In other words, the sleeve 50 controls the amount of resection. This is accomplished by appropriately sizing the platform 56. As the platform 56 decreases in size, the more material is resected. The arm 54 is adapted to engage the groove 46 such that the sleeve 50 is removably attached or temporarily affixed to the shaft 42. Although the arm 54 engages the groove 46, the sleeve 50 is still free to rotate relative to the reamer 40.

While the embodiment depicted in FIG. 9 includes the arm 54, those skilled in the art would understand that other methods of removably attaching the sleeve 50 to the reamer 40 may be used. For example, a C-clip may be used to engage the groove 46 and connect the sleeve 50 to the reamer 40.

Figure 10:
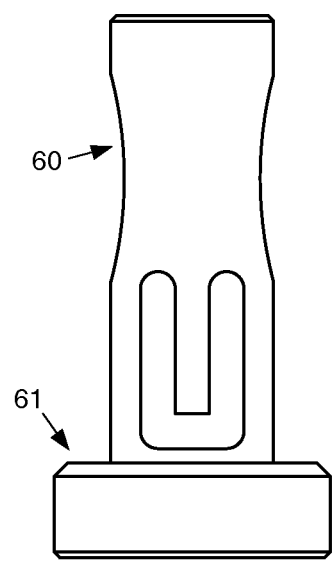
FIG. 10 is a front view of a reamer sleeve in a second embodiment.
Figure 11:
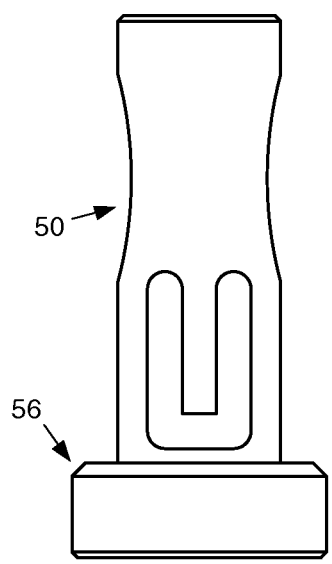
FIG. 11 is a front view of the first embodiment of the reamer sleeve.
Figure 12:
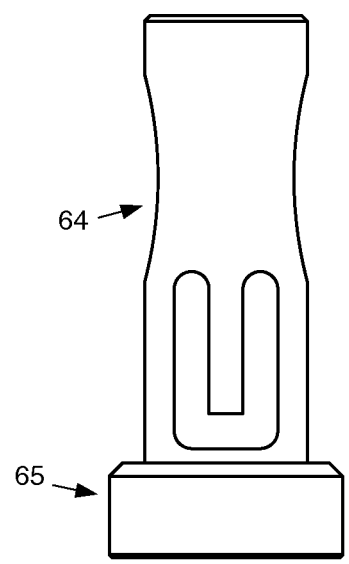
FIG. 12 is a front view of a reamer sleeve in a third embodiment.

FIGS. 10-12 illustrate alternative embodiments of the reamer sleeve. FIG. 10 illustrates an undersized reamer sleeve 62. As used herein, the term "undersized" refers to the degree or volume of bone resection, and the undersized reamer sleeve 62 has a platform 63 with a diameter larger than that of the standard size platform 56. FIG. 11 illustrates the standard reamer sleeve 50. The standard reamer sleeve 50 includes the standard size platform 56. FIG. 12 illustrates an oversized reamer sleeve 64. As used herein, the term "oversized" refers to the degree or volume of bone resection, and the oversized reamer sleeve 64 has a platform 65 with a diameter smaller than that of the standard size platform 56.

Figure 13:
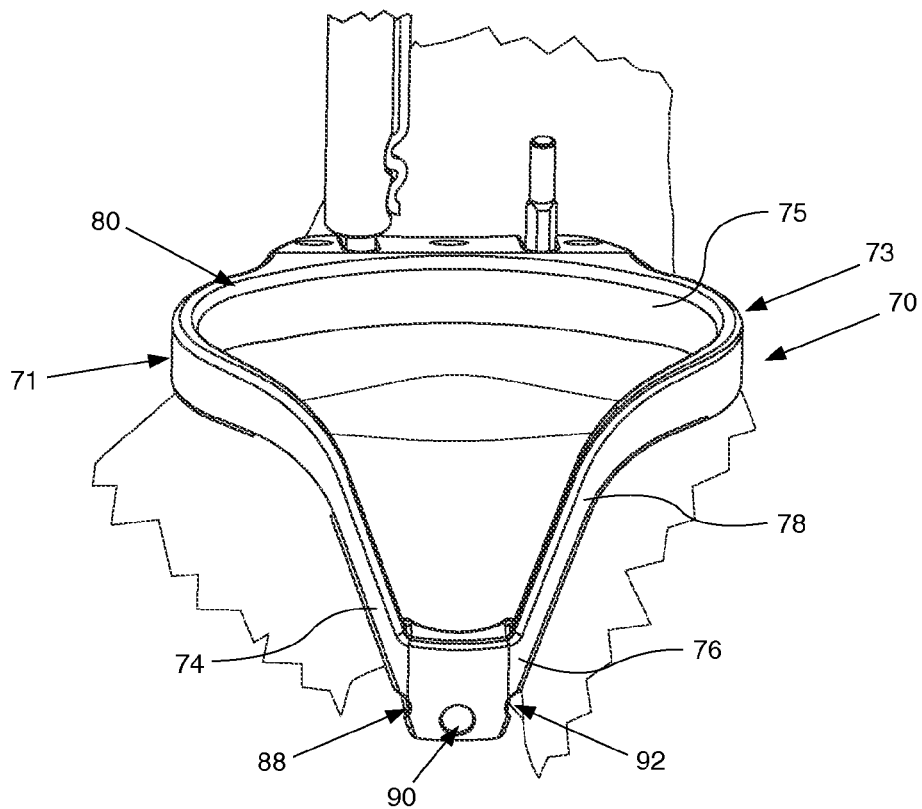
FIG. 13 is a perspective front view of a second embodiment of the reamer guide.
Figure 14:
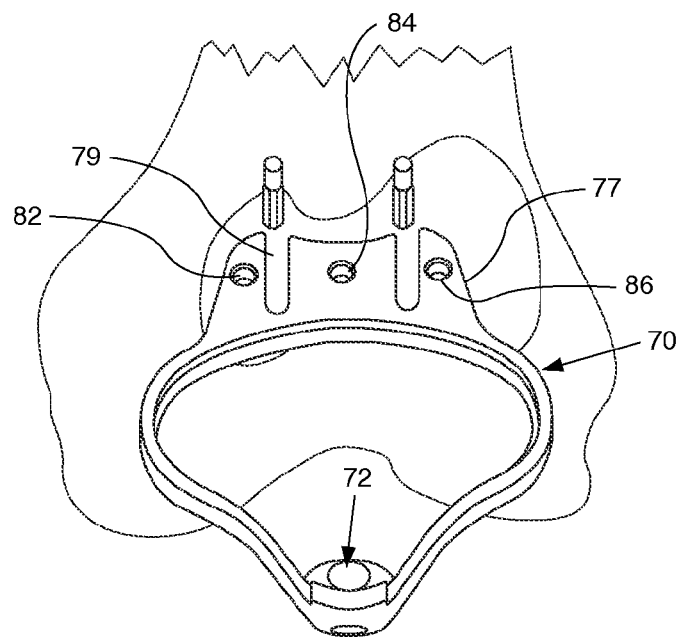
FIG. 14 is a perspective top view of the reamer guide shown in FIG. 13.

FIGS. 13 and 14 illustrate a second embodiment of the reamer guide, generally indicated by reference numeral 70. The reamer guide 70 may be used with either the first embodiment of the reamer 30 or the second embodiment of the reamer 40. The reamer guide 70 includes a first arcuate portion 71, a second arcuate portion 73, a wall 75, a protrusion 77, at least one slot 79, a first leg 74, a second leg 78, a distal tip portion 76, and a more-than-hemispherical depression or cup 72. In some embodiments, the reamer guide 70 includes a lip 80. The lip 80 and the wall 75 are shaped to match the curvature of the implant 10. The cup 72 is adapted to receive the connector 49 of the reamer 40. The cup 72 is located at a fixed depth and is over hemispherical so the tip portion 48 of the reamer 40 cannot pop out or easily slide out when the trochlear region is being reamed. In some embodiments, the reamer guide 70 includes a first hole 82, a second hole 84, a third hole 86, a fourth hole 88, a fifth hole 90, and a sixth hole 92.

The reamer guide 70 may be adapted for use with a left knee or a right knee. As such, the reamer guide 70 would limit the movement of the reamer 30, 40 so that the appropriate amount of the trochlear region is removed. In the case of the universal reamer guide, the user must be careful not to overly resect the trochlear region and caution must be exercised to limit the amount of resected bone.

In use, the reamer guide 70 is mounted to a distal end of a resected femur. A user inserts the connector 49 into the cup 72. The user levers or pivots the reamer 40 downward onto the reamer guide 70, resecting bone as the reamer 40 is pivoted. The reamer 40 is pivoted until the bearing or platform 56, 61, 63, 65 rides on or rotates against the lip 80 of the wall 75. The reamer 40 is then moved medial-to-lateral, or vice versa, to prepare the trochlear region.

Figure 15:
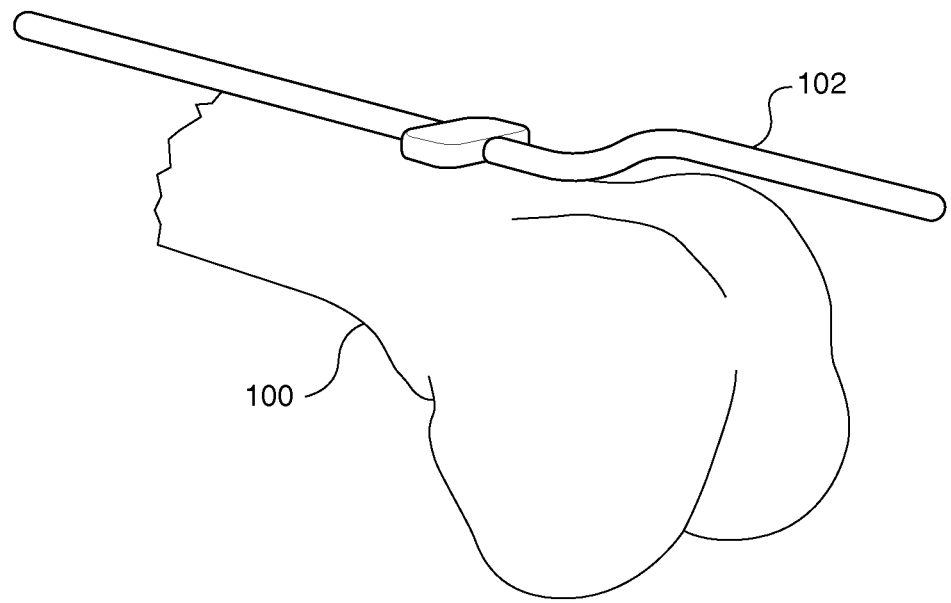
FIG. 15 is a front perspective view of a femur and a femoral extramedullary alignment rod.
Figure 16:
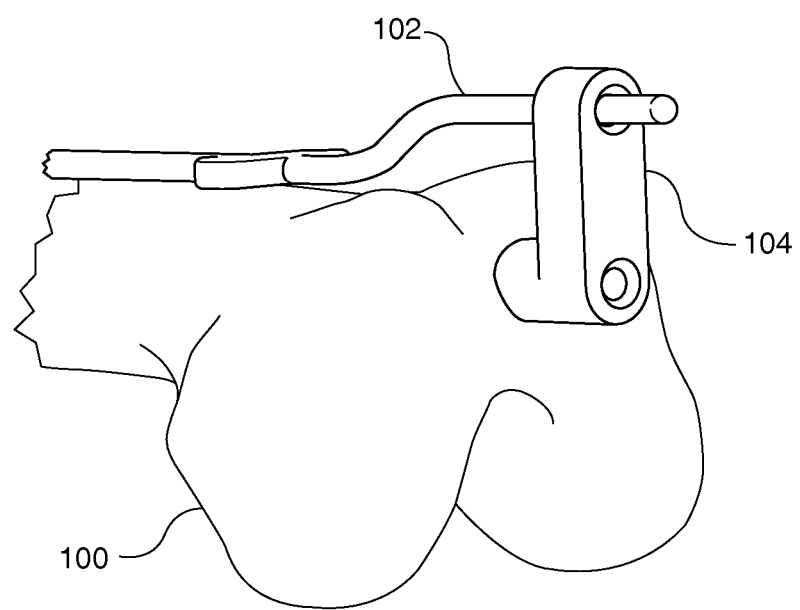
FIG. 16 is a front perspective view of the femur and a drill guide.
Figure 17:
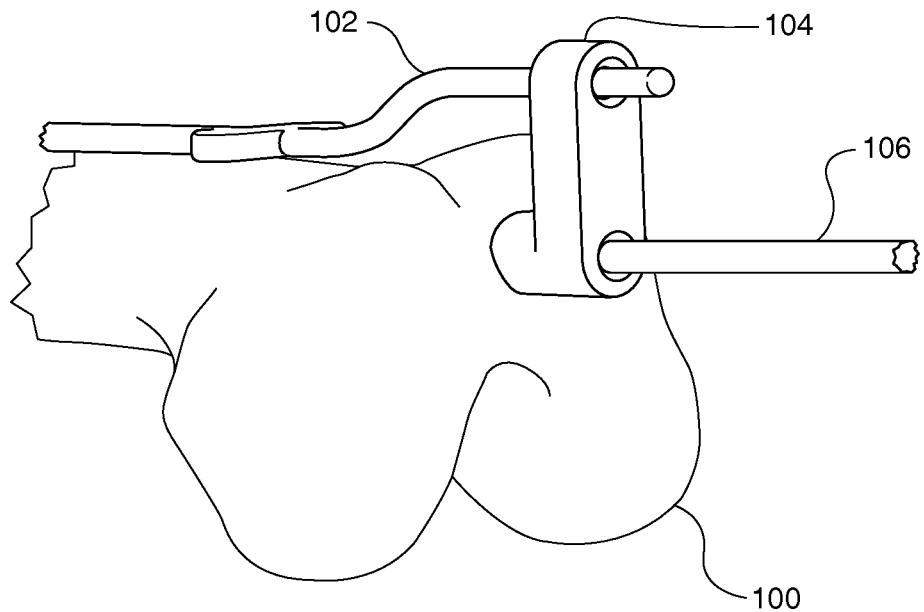
FIG. 17 is a front perspective view of the femur and a drill.
Figure 18:
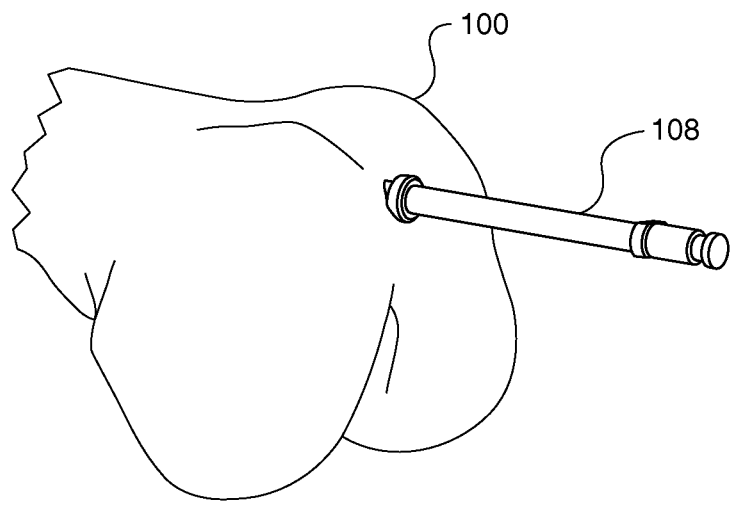
FIG. 18 is a front perspective view of the femur and an intramedullary rod.
Figure 19:
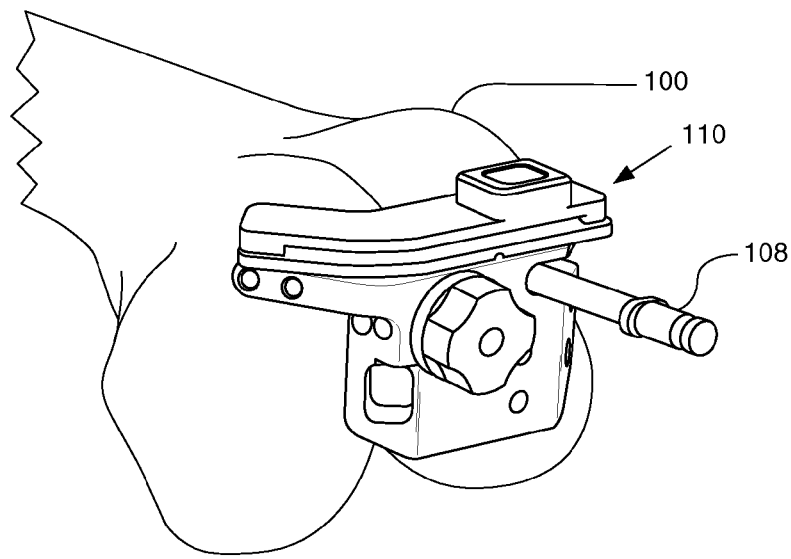
FIG. 19 is a front perspective view of the femur and an anterior cutting guide.
Figure 20:
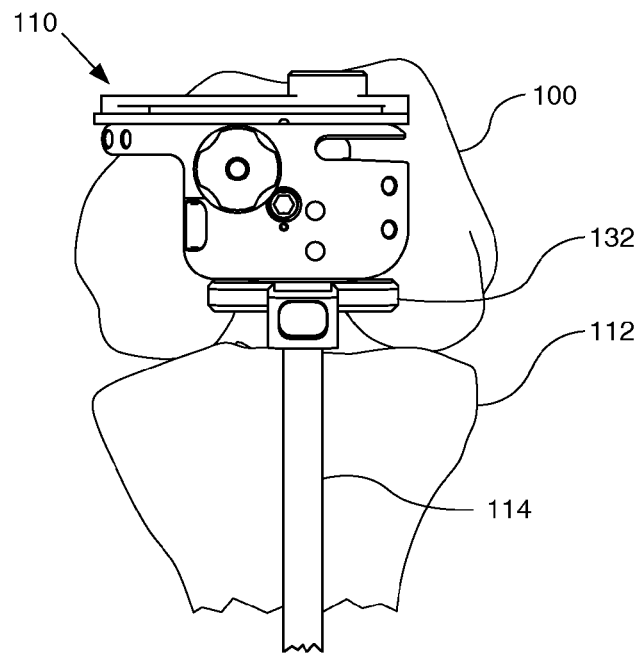
FIG. 20 is a front view illustrating the femur, a tibia, and an extramedullary up rod.
Figure 21:
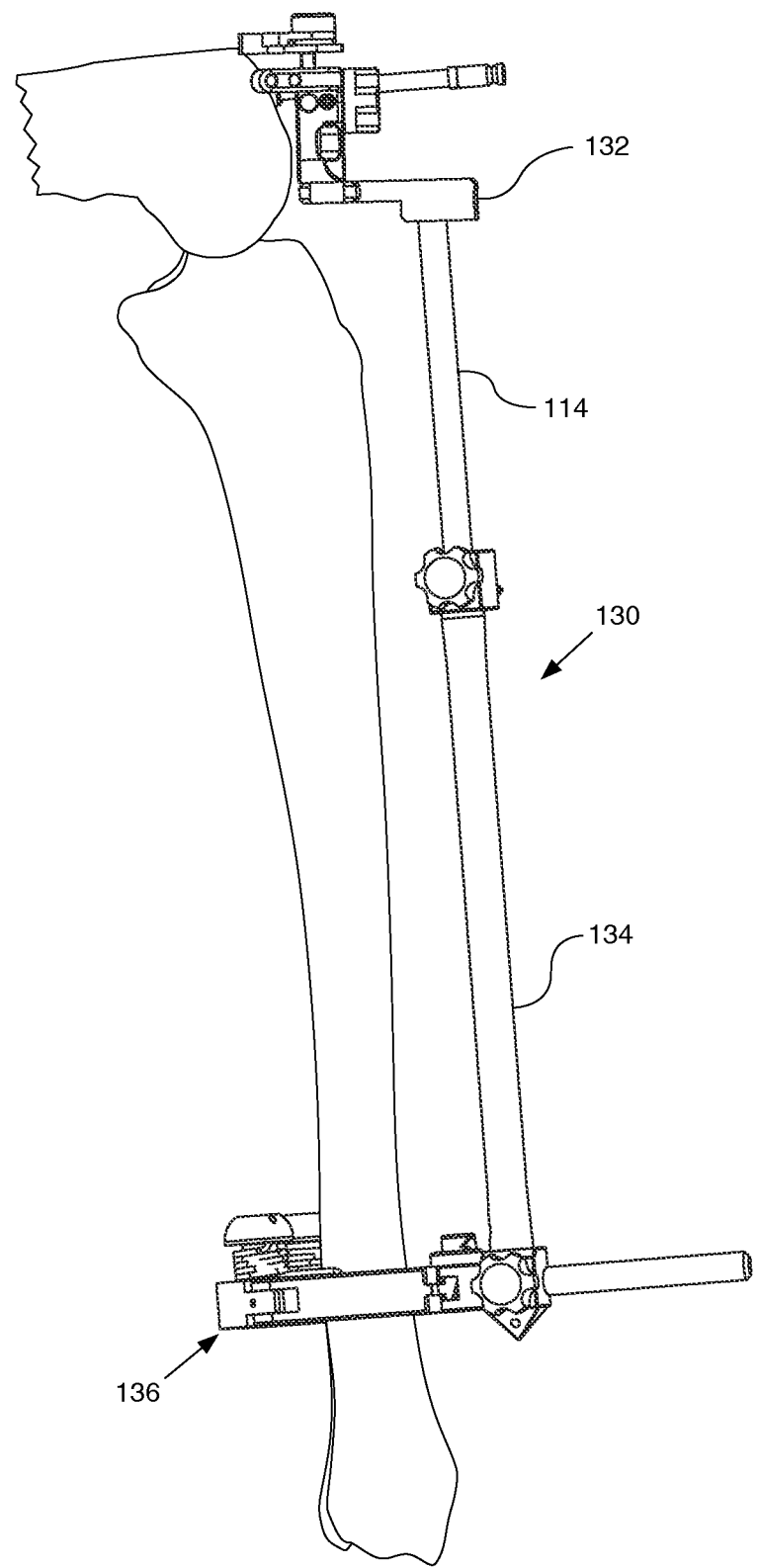
FIG. 21 is a side view of the femur, the tibia, and an extramedullar guide assembly.

FIGS. 15-38 illustrate preparation of the femur 100 and installation of the implant 10. FIG. 15 illustrates the femur 100 and a femoral extramedullar/alignment rod 102. As best seen in FIG. 16, an intramedullary drill guide 104 is connected to the femoral extramedullary alignment rod 102. In the depicted embodiment, the center-to-center distance between the holes is about twenty-six millimeters. FIG. 17 illustrates a drill 106 being inserted into the drill guide 104 in order to drill through cortical bone to the intramedullary canal. After a hole is drilled into the intramedullary canal, FIG. 18 illustrates an intramedullary rod 108 being inserted into the canal. The rod 108 may be thin to reduce damage to the intramedullary canal during insertion. As best seen in FIG. 19, an anterior cutting guide 110 is connected to the intramedullary rod 108 and placed next to the end of the femur 100. The cutting guide 110 fits over the thin intramedullary rod 108 affixed through the intramedullary canal of the femur 100. The cutting guide 110 is medially biased to fit into a minimally invasive incision. The anterior cutting guide 110 is designed with adjustable height so that a user can achieve the proper resection level.

After the cutting guide 110 is placed over the rod 108, there are two methods which may be used to orient the anterior cutting guide 110. The methods may be used separately or in combination. For example, both methods may be performed to confirm the results of whichever method was performed first. In a first method, best seen in FIGS. 20 and 21, an extramedullary guide assembly 130 is attached to a tibia 112. The extramedullary guide assembly 130 includes an extramedullary up rod 114, a tibial extramedullary guide platform 132, an extramedullary tibial down rod 134, and an ankle clamp 136. The ankle clamp 136 is attached to the distal portion of the tibia 112, and the extramedullary up rod 114 is extended upwardly until the extramedullary guide platform 132 contacts a bottom portion of the anterior cutting guide 110. The platform 132 properly orients the cutting guide 110, and thereafter the cutting guide 110 can be adjusted to achieve the proper height for the resection plane.

Figure 22:
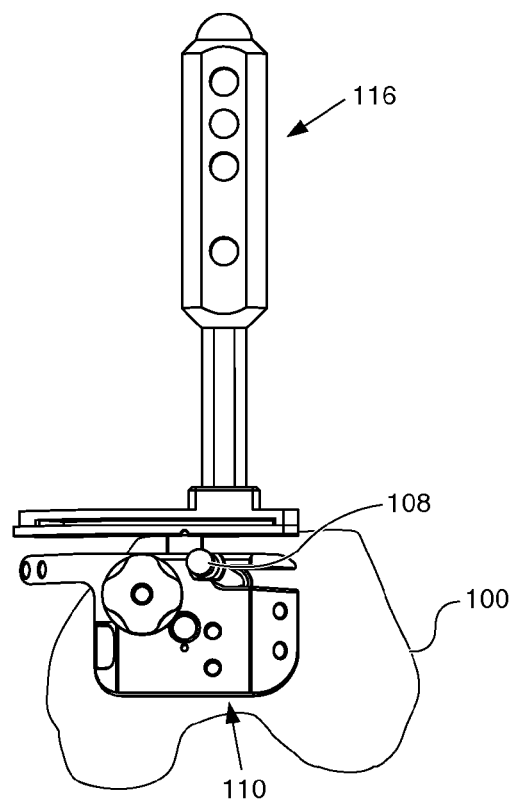
FIG. 22 is a front view illustrating the femur and a handle.
Figure 23:
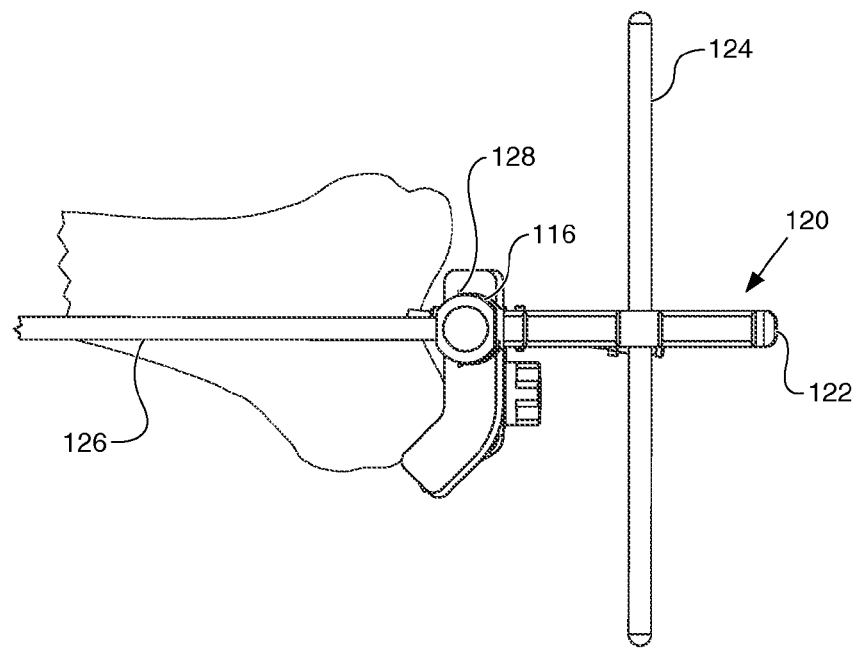
FIG. 23 is top view of the femur and an alignment bar assembly.
Figure 24:
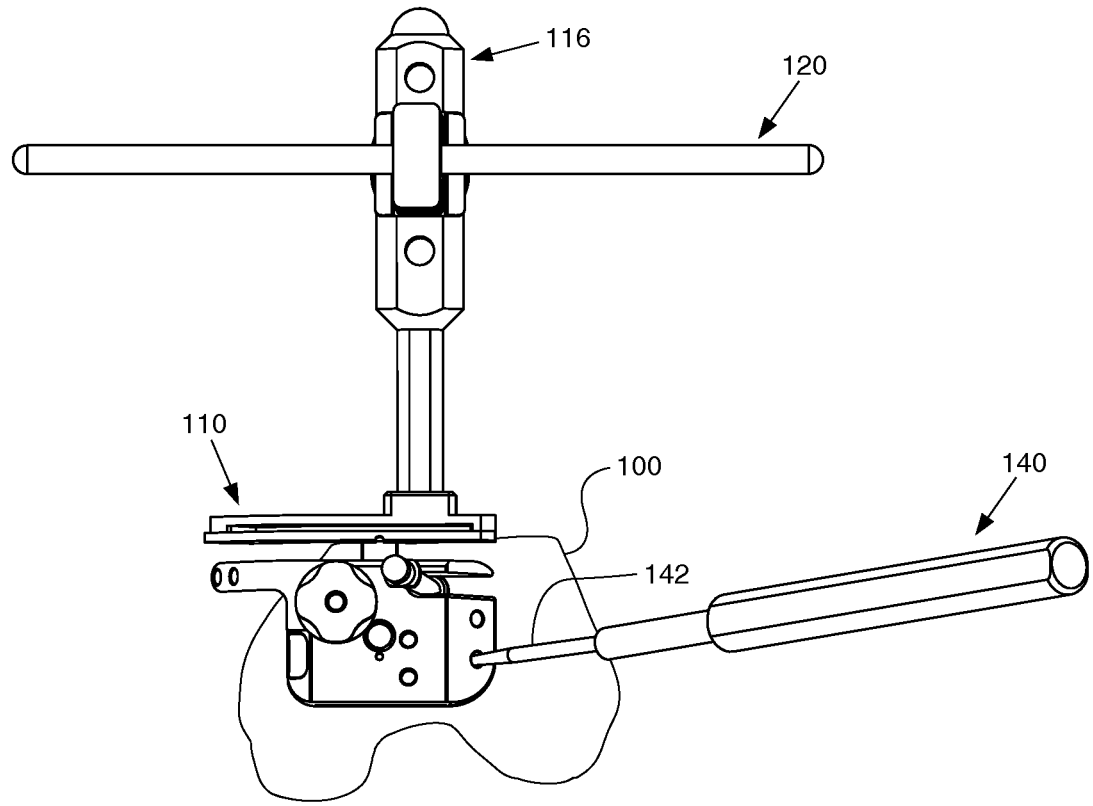
FIG. 24 is a front view of the femur and a first punch.

In a second method to orient the cutting guide 110, best seen in FIGS. 22-24, a handle 116 is attached to the anterior cutting guide 110 and an alignment bar assembly 120 is attached to the handle 116. As an example only, the handle 116 may be a quick connect handle that includes a quick release mechanism. The alignment bar assembly 120 includes a grip 122, a first alignment bar rod 124, a second alignment bar rod 126, and an alignment bar clip 128. The first alignment bar rod 124 is positioned such that it is parallel to the epicondyles. The second alignment bar rod 126 is positioned such that it is parallel to the mechanical axis of the femur. The grip 122 may be connected to the handle 116 through the use of the alignment bar clip 128. Once the first alignment bar rod 124 and the second alignment bar rod 126, and thereafter the cutting guide 110 can be adjusted to achieve the proper height for the resection plane.

Once the anterior cutting guide 110 is properly positioned, the anterior cutting guide 110 is pinned into place. FIG. 24 illustrates the anterior guide 110 being pinned into place using a first punch 140 and a first pin 142. One or more first pins 142 may be used to pin in place the anterior guide 110.

Figure 25:
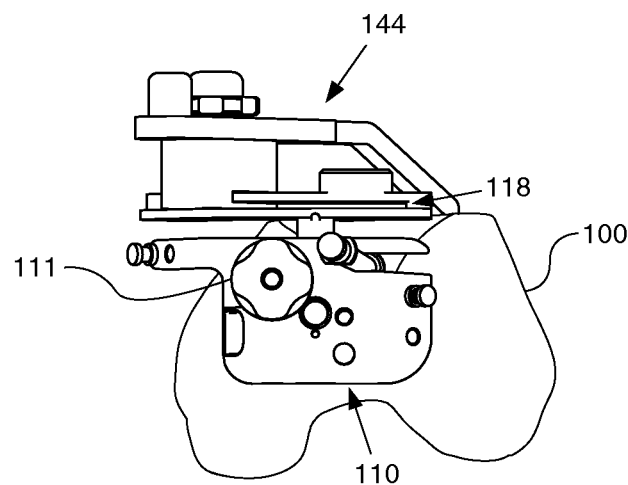
FIG. 25 is a front view of the femur and an extramedullary alignment device.
Figure 26:
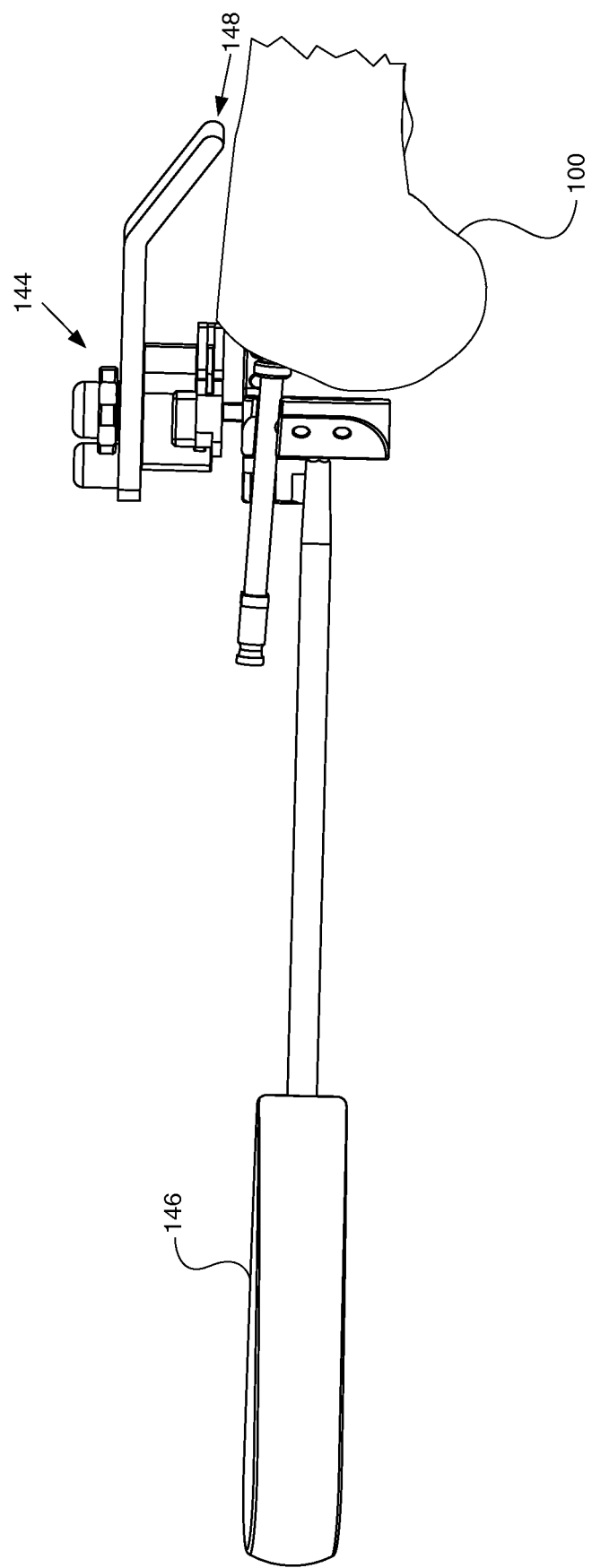
FIG. 26 is side view of the femur and a locking handle.
Figure 27:
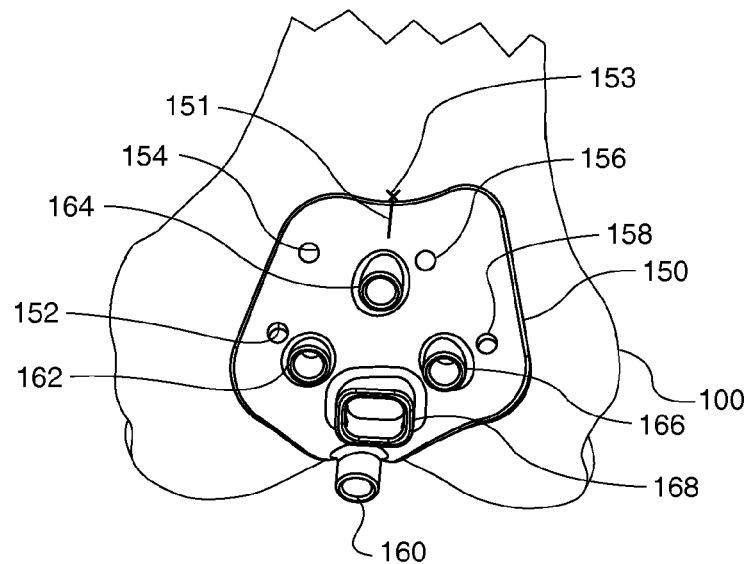
FIG. 27 is a top perspective view of the femur and a drill guide.
Figure 28:
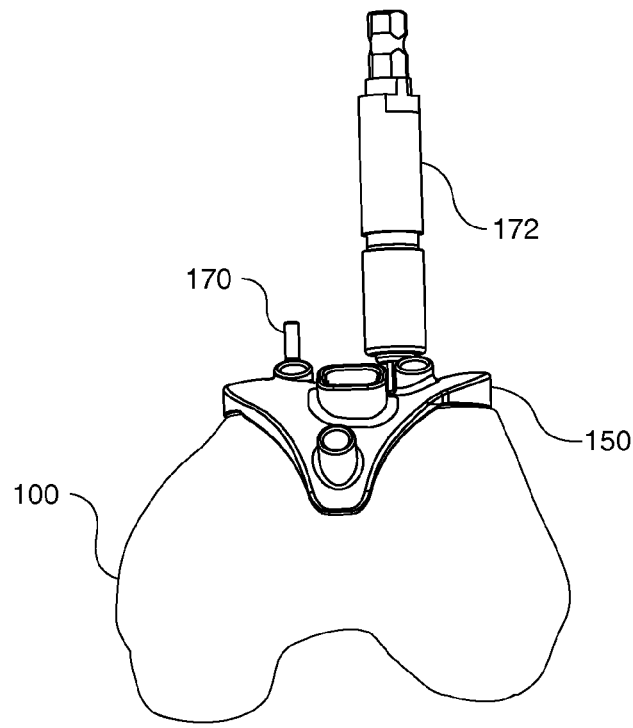
FIG. 28 is a front view of the femur, drill guide, bone pins, and bone pin insertion tool.

After the anterior cutting guide 110 is pinned, an anterior stylus 144 is connected to the anterior cutting guide 110, as best seen in FIG. 25, to set the height of the resection plane. A knob 111 of the anterior cutting guide 110 is rotated until a tip portion 148 of the anterior stylus 144 rests upon the femur 100. Once the proper resection level is set, the height of a saw guide 118 is locked into place. FIG. 26 illustrates an exemplary method of temporarily fixating the saw guide 118 wherein a locking handle or screwdriver 146 is used to rotate a set screw (not shown) in the anterior cutting guide 110. Thereafter, the anterior portion of the femur 100 is resected to achieve the generally planar surface 190 (best seen in FIG. 31). In the depicted embodiment, the anterior cut is made in three degrees of flexion to allow proper orientation of the implant 10.

After the anterior cut is made, a patello-femoral drill guide 150 mounted to the femur 100. FIGS. 27-30 illustrate the patello-femoral drill guide 150. The patello-femoral drill guide 150 includes a first pin hole 152, a second pin hole 154, a third pin hole 156, a fourth pin hole 158, a first drill guide hole 160, a second drill guide hole 162, a third drill guide hole 164, a fourth drill guide hole 166, and a receptacle or receiver 168.

Figure 29:
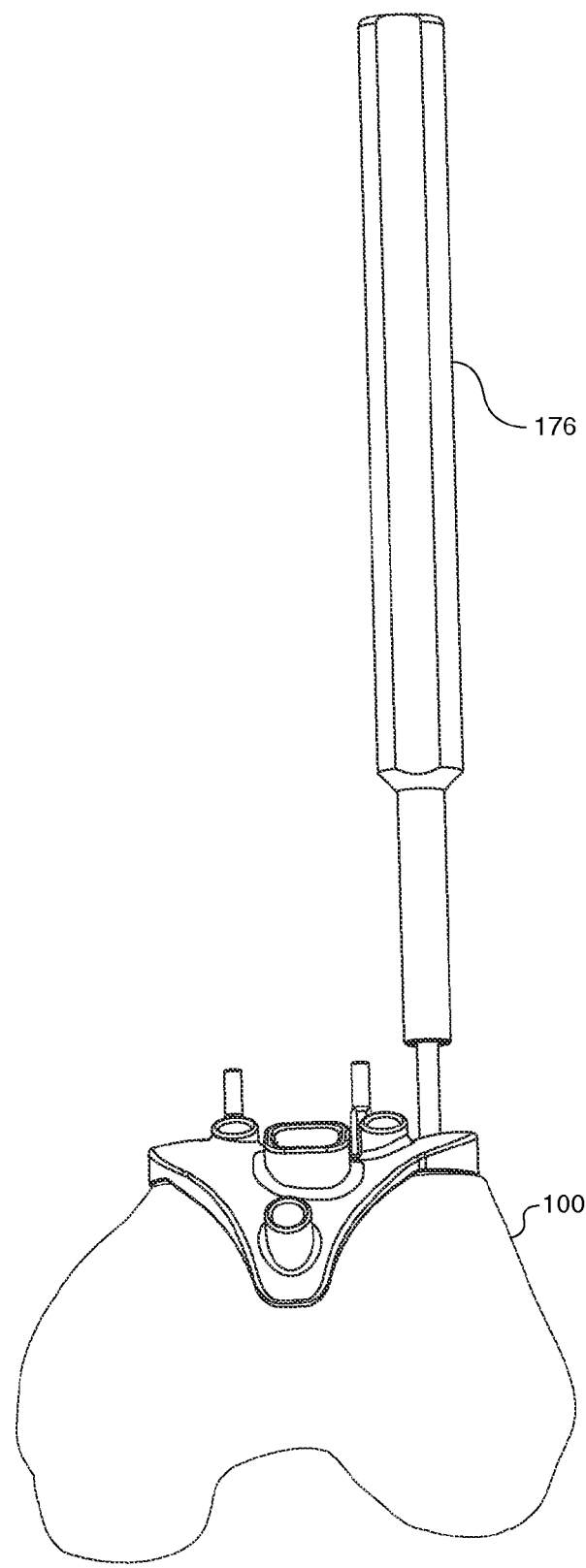
FIG. 29 is a front view of the femur, drill guide, and a second pin punch.
Figure 30:
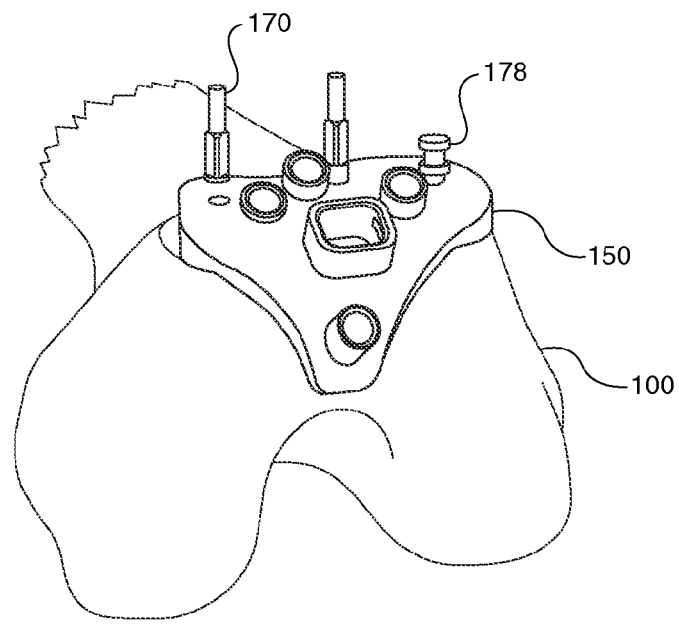
FIG. 30 is a front perspective view of the femur, the drill guide, and temporary fixation pins.

Once the patello-femoral drill guide 150 is placed on the femur 100, it is pinned into place. In the embodiment depicted in FIG. 28, one or more second pins 170 are driven into place through the use of a first pin driver 172. Second pins 170 may be headed or non-headed. In the depicted embodiments, second pins 170 are placed in second pin hole 154 and third pin hole 156. Optionally, additional fixation pins may be used to temporarily affix the patello-femoral drill guide 150 to the femur 100. For example, as best seen in FIG. 29, a second pin driver 176 may be used to install a third fixation pin 178. Thereafter, an outline of the trochlear region of the implant 10 is traced on the cartilage and/or bone from the patello-femoral drill guide 150. The outline may be achieved through the use of a cauterizer or methylene blue. For example, a user may trace the edges of the patello-femoral drill guide 150 with the cauterizer to mark the cartilage and/or bone. Additionally, the patello-femoral drill guide 150 has an indicator 151, such as a line or a triangle. A mark 153, such as a line or "X," must be placed on the femur 100 in order to reinstall the patello-femoral drill guide 150 at a later time.

Alternatively, the patello-femoral drill guide 150 is not fixed to the femur 100 when outlining or marking the trochlear region. Instead, the patello-femoral drill guide 150 is merely held in place, such as through the use of the handle 116, and the cartilage and/or bone is marked by tracing the outline of the patello-femoral drill guide 150.

After the trochlear region is outlined or marked, the patello-femoral drill guide 150 is removed and a reamer guide, such as the first embodiment 20 or the second embodiment 70, is temporarily affixed to the anterior cut surface of the femur 100. In the embodiment depicted in FIGS. 31 and 32, the non-headed pins 170 have not been removed. As such, the reamer guide 20 is placed over the pins 170, or the reamer guide 70 is slid into place such that the non-head pins 170 enter the slots 79. In some embodiments, the second pins 170 are headed, the reamer guide 70 is slid into place such that the pins 170 enter the slots 79, and the headed pins are tapped downwardly to lock the reamer guide 70 in place. The reamer guide 20, 70 contacts the resection plane 190 and is slid back until a leg 28, 74, 78 contacts the intracondylar notch. Thereafter, the reamer guide 20, 70 is pinned to the femur 100. In the embodiment depicted in FIG. 32, a third pin 208 is inserted into the hole 82 and a fourth pin 210 is inserted into the hole 92, but other pin and hole combinations may be used. Although three pins are shown near the distal tip portion 26, 76, only one pin may be used as the axis of each hole 88, 90, 92 is coplanar with the other holes.

After the reamer guide 20, 70 is pinned, the trochlear region is reamed. In the embodiment depicted in FIGS. 33 and 34, the reamer 40 and the sleeve 50 are used to resect the trochlear region. The reamer 40, or alternatively the reamer 30, is moved from side-to-side to ream the trochlear region. If the reamer guide is universal, the user must exercise care to only ream up until the outline or mark on the cartilage and/or bone. However, if the reamer guide is constructed and arranged for use only on a single side, the reamer 30, 40 may be moved from side-to-side until the reamer contacts one of the arcuate portions 21, 23, 71, 73.

In some methods, the trochlear region is not reamed with a reamer but is merely prepared with a rasp, osteotome, or other sharp tool.

Figure 35:
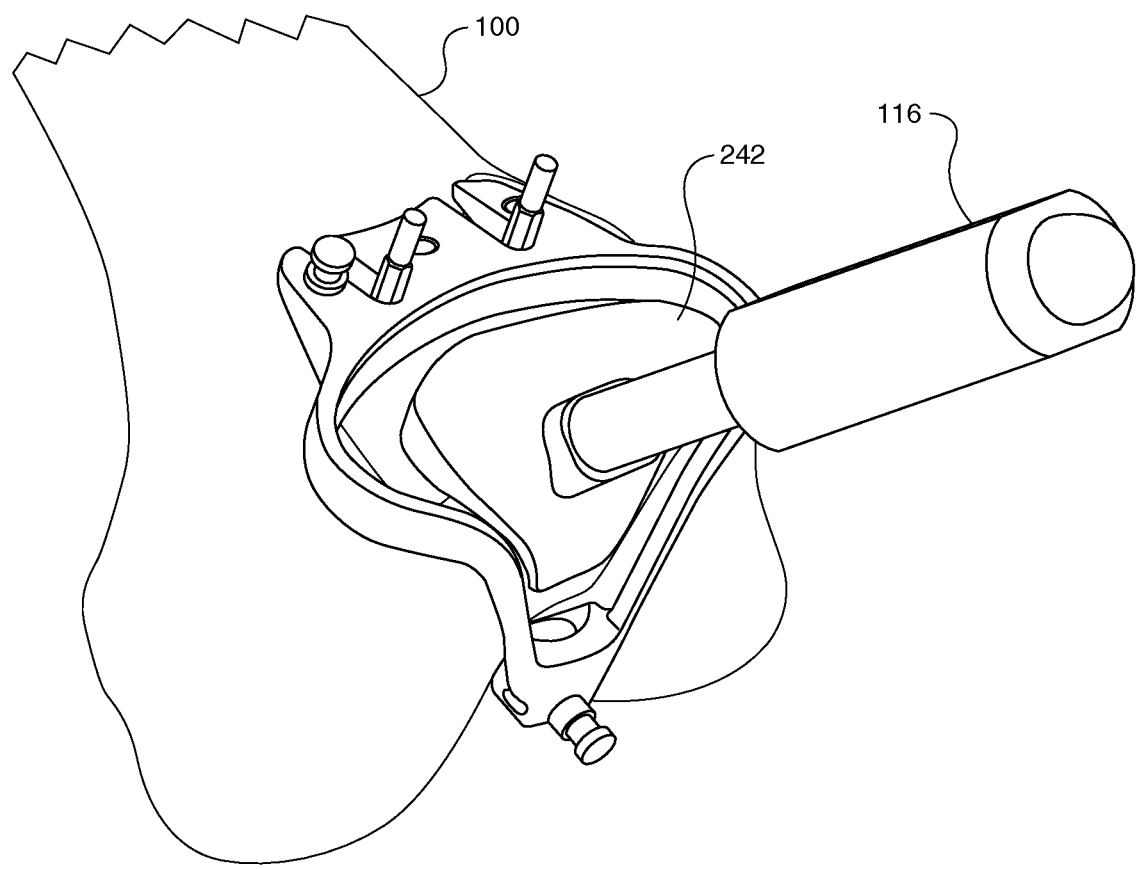
FIG. 35 is a top perspective view of the femur, a depth gauge, and a handle.

After the trochlear region is reamed, it is necessary to verify the depth of the reaming. As best seen in FIG. 35, a depth gauge 242 is used to check the depth of the resection. The depth gauge 242 may be left-hand, right-hand, or universal. In the depicted embodiment, the depth gauge 242 is designed for use only a single side (e.g., left-hand). The depth gauge 242 may be adapted for a particular size of implant or it may be designed for use across an entire series of implants. In the depicted embodiments, the implants are all of the same thickness, regardless of size. In other words, implants may grow in width and length as they increase in size but do not increase in thickness, and, therefore, it is possible to have one depth gauge per side for a series of implants. When checking the depth of the ream, it is important that there is a smooth transition between the cartilage in the intracondylar notch and the depth gauge 242. If the depth gauge 242 is raised above the remainder of the trochlear region, it will be necessary to ream to an additional depth. This is accomplished by reaming with a reamer having a smaller bearing than previously used, by reaming with a reamer having a larger flute than previously used, or by reaming with a sleeve that has a smaller diameter platform than was previously used. However, if the depth gauge is at or below the remainder of the trochlear region, the depth of the ream is sufficient. In some embodiments, the handle 116 is attached to the depth gauge 242 for ease of use and manipulation.

Figure 36:
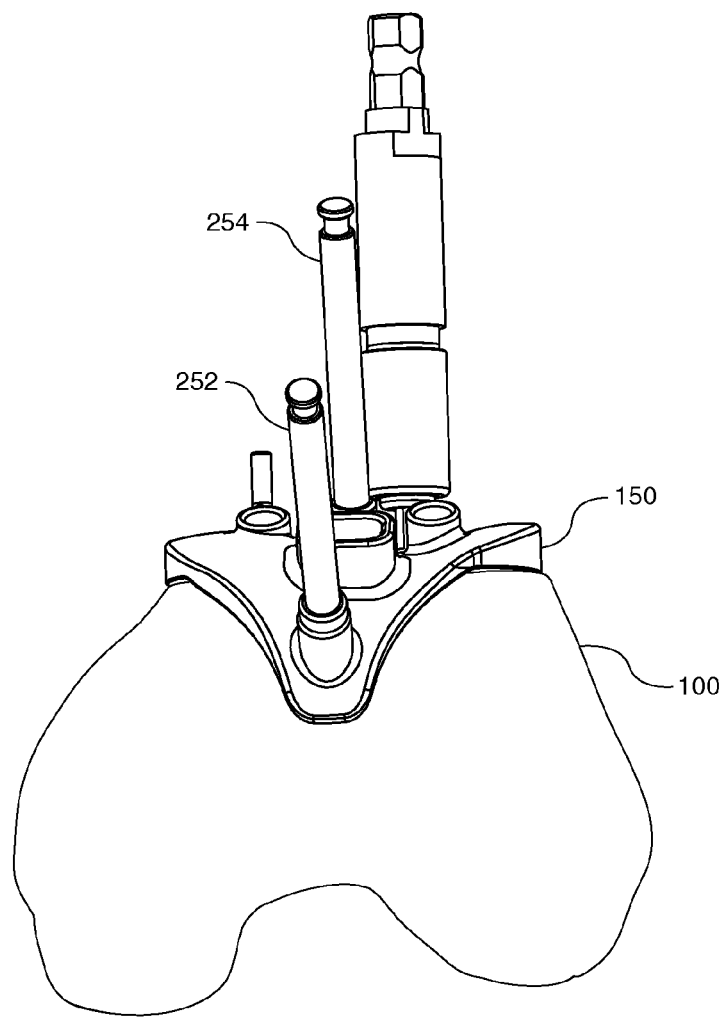
FIG. 36 is a front view of the femur, the drill guide, peg drill, and fixation pegs.

After the depth of the ream is verified, the pins and the reamer guide are removed, and the patello-femoral drill guide 150 is reinstalled for drilling of the anterior and/or distal peg holes. FIG. 36 illustrates reattachment of the drill guide 150.

The intracondylar notch portion of the patello-femoral drill guide 150 is placed in the reamed trochlear region, and the mark 153 on the femur 100 is aligned with the indicator 151 on the patello-femoral drill guide 150. Thereafter, the patello-femoral drill guide 150 is pinned into place through the use of one or more fixation pins. After the patello-femoral drill guide 150 is located and pinned, one of the holes is drilled. A drill guide alignment post 252 is placed in the drilled hole to stabilize the construct. Then, a second hole is drilled, and another drill guide alignment post 254 is placed in the second drilled hole for additional stability. Optionally, additional alignment posts may be used for stability. Thereafter, the remaining holes are drilled. The patello-femoral drill guide 150 and the fixation pins are then removed.

Figure 37:
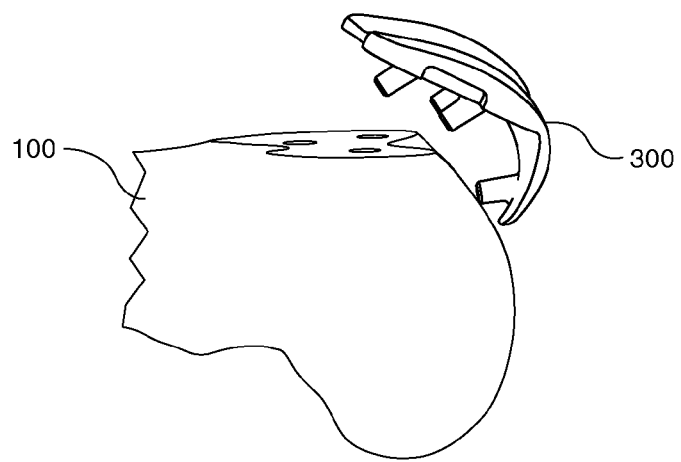
FIG. 37 is a side perspective illustrating the femur and a trial.

FIG. 37 illustrates a trial 300 being placed on the femur 100. A user utilizes the trial 300 to test patellar tracking as well as the fit and articulation of the revised knee. The user may need to adjust the size of the trial 300 or its location to perfect the revised knee. The trial 300 generally snaps into place, but an impactor may be used to positively locate the trial 300.

Figure 38:
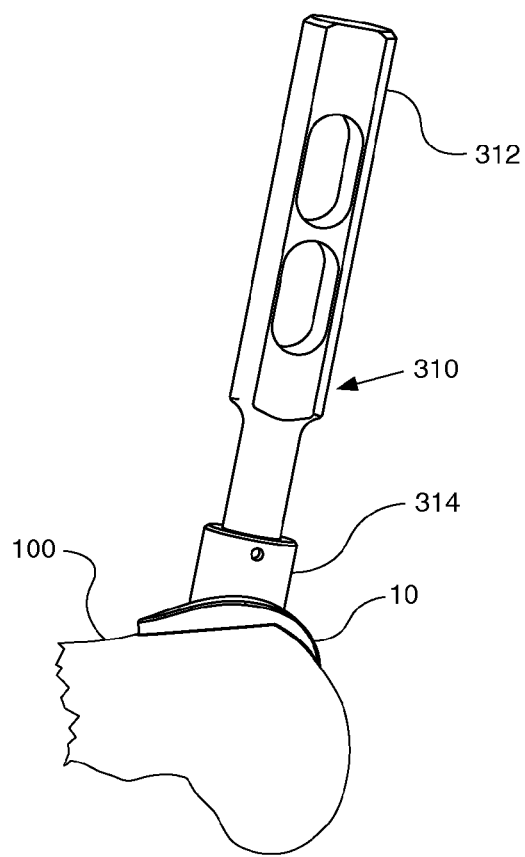
FIG. 38 is a side view of the femur, the implant, and an impactor.

FIG. 38 illustrates the implant 10 being installed with the use of an impactor 310. The impactor 310 includes an impactor handle 312 and a bumper 314. In some embodiments, bone cement may be applied to the underside of the implant 10 prior to installation.

The invention also includes a method of installing an asymmetric patello-femoral implant. The method includes the step of: (1) resecting a femur; (2) reaming a distal portion of the femur; (3) attaching a patello-femoral drill guide to the femur; and (4) installing the implant. The step of resecting the femur may include the step of attaching an anterior cutting guide to the femur. The step of reaming the distal portion of the femur may include the steps of attaching a reamer guide to the femur, rotatably connecting a reamer to the reamer guide, and moving the reamer relative to the reamer guide in order to ream the distal end of the femur. Further, the step of reaming the distal portion of the femur may include attaching a reamer sleeve to a reamer. Additionally, the step of reaming the distal portion of the femur may include verifying the depth of the ream with a depth gauge. The step of attaching a patello-femoral drill guide to the femur may include the steps of marking an outline of the patello-femoral drill guide on cartilage and/or bone and the step of placing a mark on the femur. Further, the step of attaching a patello-femoral drill guide to the femur may include the step of drilling a plurality of holes in the femur. The step of installing the implant may include the steps of placing bone cement on the implant or the femur, placing pegs of the implant into drilled holes in the femur, and striking an impactor to seat the implant on the femur.

A kit may be provided. The kit may include one or more of the following items: a reamer, a reamer guide, a depth gauge, a trial, and an implant. Optionally, the kit may also include one or more standard reamer sleeves, oversized reamer sleeves, or undersized reamer sleeves.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

Figure 33:
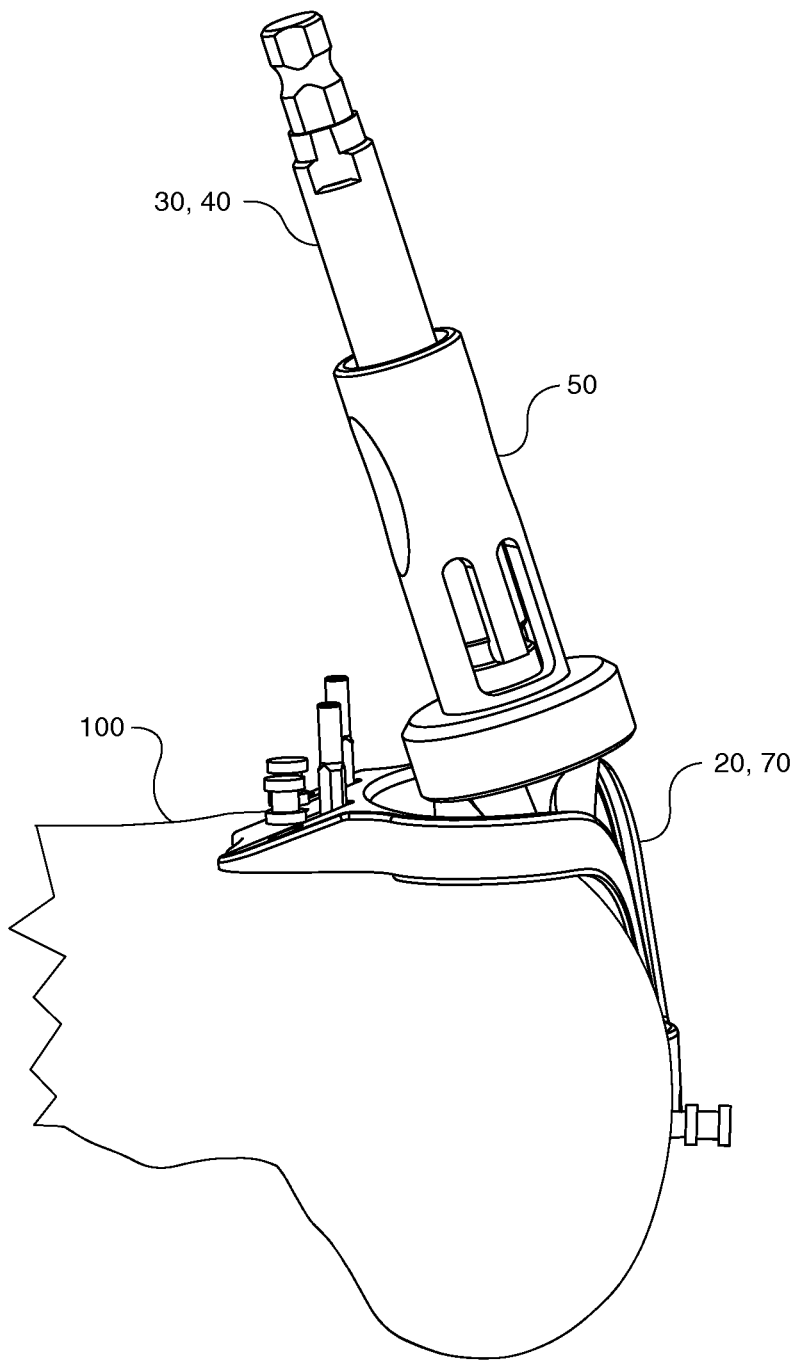
FIG. 33 is a side view of the femur, the second embodiment of the reamer guide, and the second embodiment of the reamer.
Figure 34:
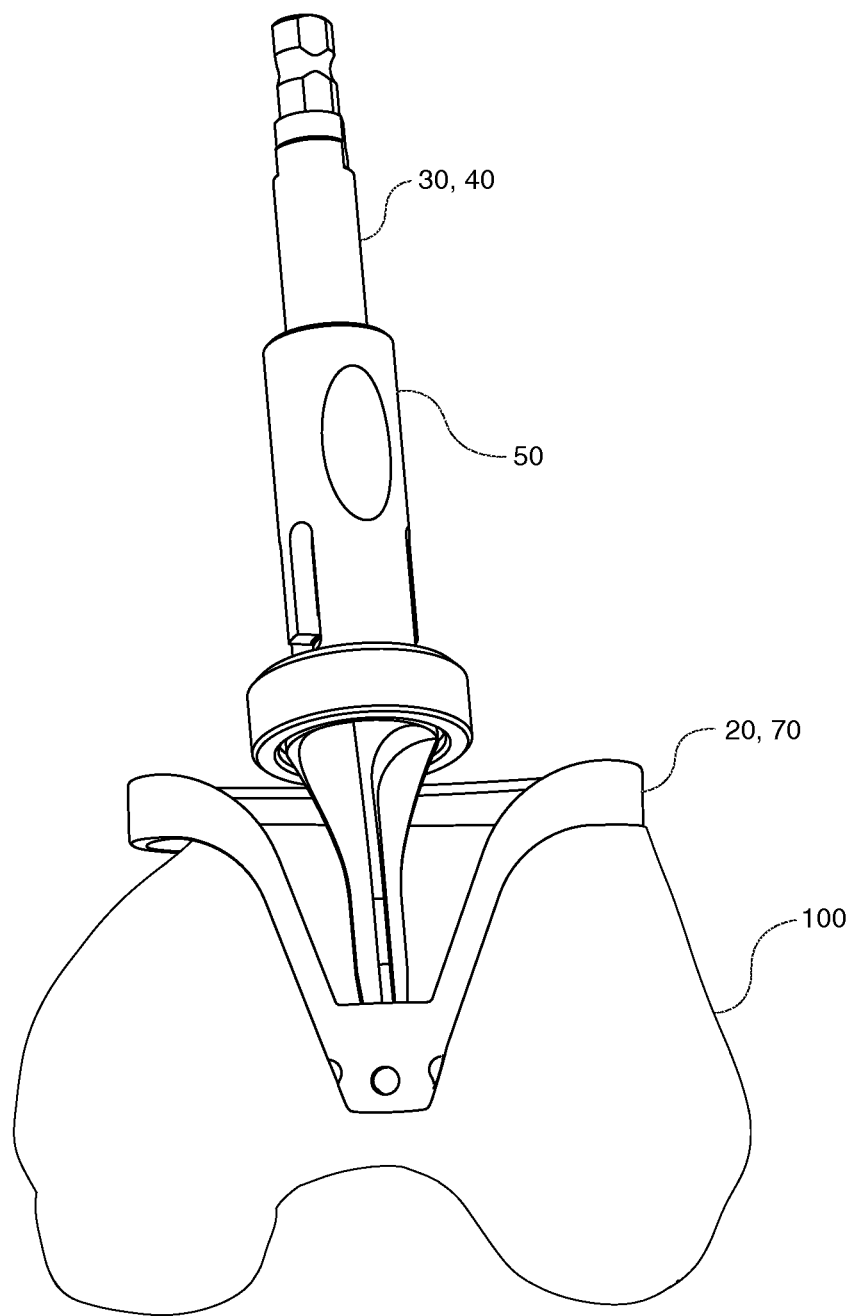
FIG. 34 is a front view of the components shown in FIG. 33.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while FIGS. 33 and 34 illustrate the use of a reamer in combination with a reamer sleeve, it should be understood that reamers without sleeves are equally acceptable. Thus, the breadth and scope of the present invention should not be limited by any of the above-described exemplary embodiments, but should be defined only in accordance with the following claims appended hereto and their equivalents.

What is claimed is:

1. A method of preparing a femur for a patello-femoral implant, comprising the steps of:
   a. cutting a planar anterior surface on the femur;
   b. attaching a reamer guide to the planar anterior surface, the reamer guide having a wall portion, a leg connected to the wall portion, and a distal tip portion connected to the leg;
   c. connecting a reamer to the distal tip portion of the reamer guide; and
   d. reaming a portion of a trochlea by translating the reamer medially or laterally along the wall portion of the reamer guide, wherein the step of reaming includes pivoting a portion of the reamer about the distal tip portion of the reamer guide.

2. The method of claim 1, further comprising a step of setting the depth of the reaming step.

3. The method of claim 2, wherein the step of setting the depth comprises providing a sleeve to the reamer, the sleeve having a bearing surface which has a diameter, the diameter of the bearing surface sets the depth of the reaming step.

4. The method of claim 1, further comprising the steps of:
   a. placing a drill guide over the planar anterior surface and reamed portion of the femur;
   b. drilling a hole for an anterior peg on the planar anterior surface of the femur; and
   c. drilling a hole for a distal peg on a distal surface of the femur wherein the drill guide sets the position and orientation of the holes for the anterior peg and the distal peg such that the anterior peg and distal peg are not parallel.

5. The method of claim 1, wherein the planar anterior surface is angled with respect to the coronal plane.

6. The method of claim 5, wherein the planar anterior surface is angled less than 10 degrees from the coronal plane.

7. A method of preparing a femur for a patello-femoral implant, comprising the steps of:
   a. cutting a planar anterior surface on the femur;
   b. attaching a reamer guide to the planar anterior surface, the reamer guide having a wall portion, a leg connected to the wall portion, and a distal tip portion connected to the leg;
   c. engaging a distal portion of a reamer with the distal tip portion of the reamer guide; and
   d. reaming a portion of a trochlea by translating the reamer along the wall portion of the reamer guide and pivoting the reamer about the distal tip portion while the distal portion of the reamer remains engaged with the distal tip portion of the reamer guide.

8. The method of claim 7, wherein the reamer guide comprises a recess in the distal tip portion of the reamer guide; and
   wherein engaging the distal portion of the reamer with the distal tip portion of the reamer guide comprises inserting a distal end of the reamer into the recess in the distal tip portion of the reamer guide.

9. The method of claim 8, wherein the reamer includes a connector having a spherical shape; and wherein inserting the distal end of the reamer into the recess in the distal tip portion comprises inserting the connector of the reamer in the recess of the reamer guide.

10. The method of claim 7, wherein reaming the portion of the trochlea by translating the reamer along the wall portion of the reamer guide while the distal portion of the reamer remains engaged with the distal tip portion of the reamer guide comprises translating a proximal portion of the reamer medially or laterally along the wall portion while the distal portion of the reamer remains engaged with the distal tip portion of the reamer guide.

11. The method of claim 10, wherein the planar anterior surface is angled less than 10 degrees from the coronal plane.

12. The method of claim 7, further comprising attaching a reamer sleeve to the reamer, the reamer sleeve being configured to engage the wall portion of the reamer guide when the distal portion of the reamer is engaged with the distal tip portion of the reamer guide to set a depth of the reaming step.

13. The method of claim 12, further comprising selecting a reamer sleeve from among a plurality of reamer sleeves each configured to set a different reaming depth when the respective reamer sleeves are engaged with the wall portion;
 wherein attaching a reamer sleeve comprises attaching the selected reamer sleeve to the reamer.

14. The method of claim 7, further comprising the steps of:
a. placing a drill guide over the planar anterior surface and reamed portion of the femur;
b. drilling a hole for an anterior peg on the planar anterior surface of the femur; and
c. drilling a hole for a distal peg on a distal surface of the femur wherein the drill guide sets the position and orientation of the holes for the anterior peg and the distal peg such that the anterior peg and distal peg are not parallel.

15. The method of claim 7, wherein the planar anterior surface is angled with respect to the coronal plane.

16. The method of claim 7, wherein reaming the portion of the trochlea by translating the reamer along the wall portion of the reamer guide comprises translating the reamer medially or laterally along the wall portion such that a portion of the reamer remains in contact with the wall portion during translation of the reamer.

17. A method of preparing a femur for a patello-femoral implant, comprising the steps of:
a. cutting a planar anterior surface on the femur;
b. attaching a reamer guide to the planar anterior surface, the reamer guide having a wall portion, a leg connected to the wall portion, and a distal tip portion connected to the leg, the distal tip portion defining a recess;
c. placing a distal end portion of a reamer in the recess in the distal tip portion of the reamer guide; and
d. reaming a portion of a trochlea by translating a proximal portion of the reamer along the wall portion of the reamer guide such that a portion of the proximal portion of the reamer remains in contact with the wall portion during translation of the proximal portion, and pivoting the distal end portion of the reamer in the recess.

18. The method of claim 17, wherein translating the proximal portion of the reamer along the wall portion of the reamer guide comprises translating the proximal portion of the reamer guide medially or laterally along a curved path defined by the wall portion.

19. The method of claim 17, wherein attaching the reamer guide to the planar anterior surface comprises attaching a reamer guide that has a curved wall portion extending between a medial arcuate portion and a lateral arcuate portion, and a generally V-shaped leg extending from the medial arcuate portion and the lateral arcuate portion to the distal tip portion.

* * * * *

UNITED STATES PATENT AND TRADEMARK OFFICE
CERTIFICATE OF CORRECTION

PATENT NO. : 8,523,869 B2
APPLICATION NO. : 11/915131
DATED : September 3, 2013
INVENTOR(S) : Christopher F. Scifert et al.

It is certified that error appears in the above-identified patent and that said Letters Patent is hereby corrected as shown below:

On the Title Page

Under "(75) Inventors:" replace "Hanando" with --Hernando--.

In the Specification

At Column 2, Line 47, replace "tracking" with --tracking.--.

At Column 3, Line 12, replace "tracking" with --tracking.--.

At Column 3, Line 45, replace "invention, hi" with --invention. In--.

At Column 4, Line 19, replace "extramedullar" with --extramedullary--.

At Column 8, Line 30, replace "extramedullary/alignment" with --extramedullary alignment--.

Signed and Sealed this
Seventeenth Day of April, 2018

Andrei Iancu
*Director of the United States Patent and Trademark Office*